United States Patent
Ochs

(10) Patent No.: US 9,861,317 B2
(45) Date of Patent: Jan. 9, 2018

(54) METHODS AND SYSTEMS FOR DETERMINING REGIONAL BLOOD OXYGEN SATURATION

(71) Applicant: Covidien LP, Mansfield, MA (US)

(72) Inventor: James Ochs, Palo Alto, CA (US)

(*) Notice: Subject to any disclaimer, the term of this patent is extended or adjusted under 35 U.S.C. 154(b) by 267 days.

(21) Appl. No.: 14/626,703

(22) Filed: Feb. 19, 2015

(65) Prior Publication Data

US 2015/0230758 A1    Aug. 20, 2015

Related U.S. Application Data

(60) Provisional application No. 61/942,568, filed on Feb. 20, 2014.

(51) Int. Cl.
  *A61B 5/1455* (2006.01)
  *A61B 5/00* (2006.01)

(52) U.S. Cl.
  CPC ........ *A61B 5/7203* (2013.01); *A61B 5/14552* (2013.01); *A61B 5/7221* (2013.01); *A61B 5/7278* (2013.01); *A61B 5/742* (2013.01); *A61B 2562/0238* (2013.01)

(58) Field of Classification Search
  CPC ... A61B 5/0002; A61B 5/0059; A61B 5/1455; A61B 5/14551; A61B 5/14552; A61B 5/14553; A61B 5/14532; A61B 5/72
  See application file for complete search history.

(56) References Cited

U.S. PATENT DOCUMENTS

| 5,115,133 A | 5/1992 | Knudson |
| 5,187,672 A | 2/1993 | Chance et al. |
| 5,204,532 A * | 4/1993 | Rosenthal ............ A61B 5/1455 250/252.1 |
| 5,222,495 A | 6/1993 | Clarke et al. |

(Continued)

OTHER PUBLICATIONS

J. Allen, "Photoplethysmography and its Application in Clinical Physiological Measurement," Physiol. Meas., vol. 28, pp. R1-R39, Mar. 2007.

(Continued)

*Primary Examiner* — Eric Winakur
*Assistant Examiner* — Chu Chuan (J J) Liu

(57) ABSTRACT

Methods and systems are presented for determining regional blood oxygen saturation ($rSO_2$) of a subject. Differential absorption values may be determined based on received first and second light signals corresponding to light attenuated by respective first and second regions of the subject. Reference absorption curves are received, each associated with an $rSO_2$ value and containing expected absorption values. The differential absorption values are compared with the expected absorption values to determine a best fit reference absorption curve. An $rSO_2$ value is determined based on the best fit reference absorption curve. An $rSO_2$ value may also be determined based on a combination of two or more $rSO_2$ estimates. The $rSO_2$ estimates are determined based on two or more pairs of the differential absorption values. The differential absorption values are determined based on received first and second lights signals corresponding to three or more wavelengths of light.

11 Claims, 11 Drawing Sheets

(56) References Cited

U.S. PATENT DOCUMENTS

| | | | |
|---|---|---|---|
| 5,277,181 A | 1/1994 | Mendelson et al. | |
| 5,299,570 A | 4/1994 | Hatschek | |
| 5,419,321 A | 5/1995 | Evans | |
| 5,440,388 A | 8/1995 | Erickson | |
| 5,482,034 A | 1/1996 | Lewis et al. | |
| 5,524,617 A * | 6/1996 | Mannheimer | A61B 5/14551 356/41 |
| 5,661,302 A | 8/1997 | Evans et al. | |
| 5,673,701 A | 10/1997 | Chance | |
| 5,747,806 A | 5/1998 | Khalil et al. | |
| 5,770,454 A | 6/1998 | Essenpreis et al. | |
| 5,803,910 A | 9/1998 | Potratz | |
| 5,820,558 A | 10/1998 | Chance | |
| 5,825,488 A | 10/1998 | Kohl et al. | |
| 5,830,132 A | 11/1998 | Robinson | |
| 5,830,133 A * | 11/1998 | Osten | A61B 5/14551 356/39 |
| 5,902,235 A | 5/1999 | Lewis et al. | |
| 5,954,053 A | 9/1999 | Chance et al. | |
| 5,983,122 A | 11/1999 | Jarman et al. | |
| 6,058,324 A | 5/2000 | Chance | |
| 6,122,535 A | 9/2000 | Kaestle et al. | |
| 6,236,047 B1 | 5/2001 | Malin et al. | |
| 6,278,889 B1 | 8/2001 | Robinson | |
| 6,353,226 B1 | 3/2002 | Khalil et al. | |
| 6,438,399 B1 | 8/2002 | Kurth | |
| 6,549,795 B1 | 4/2003 | Chance | |
| 6,615,061 B1 | 9/2003 | Khalil et al. | |
| 6,615,065 B1 | 9/2003 | Barrett et al. | |
| 6,708,048 B1 | 3/2004 | Chance | |
| 6,819,950 B2 | 11/2004 | Mills | |
| 7,098,037 B2 | 8/2006 | Haas et al. | |
| 7,187,960 B2 | 3/2007 | Abreu | |
| 7,271,912 B2 | 9/2007 | Sterling et al. | |
| 7,315,752 B2 | 1/2008 | Kraemer et al. | |
| 7,356,365 B2 | 4/2008 | Schurman | |
| 7,424,317 B2 | 9/2008 | Parker et al. | |
| 7,532,919 B2 * | 5/2009 | Soyemi | A61B 5/14551 600/323 |
| 8,821,397 B2 | 9/2014 | Al-Ali et al. | |
| 8,965,472 B2 | 2/2015 | Benni | |
| 9,326,712 B1 | 5/2016 | Kiani | |
| 2006/0211925 A1 * | 9/2006 | Lamego | A61B 5/14552 600/310 |
| 2008/0228053 A1 | 9/2008 | Wang et al. | |
| 2008/0316488 A1 * | 12/2008 | Mao | A61B 5/14553 356/432 |
| 2010/0030054 A1 * | 2/2010 | Baruch | A61B 5/14553 600/368 |
| 2011/0208024 A1 | 8/2011 | Widman et al. | |
| 2014/0371548 A1 | 12/2014 | Al-Ali et al. | |
| 2015/0099950 A1 | 4/2015 | Al-Ali et al. | |

OTHER PUBLICATIONS

W. B. Murray and P. A. Foster, "The Peripheral Pulse Wave: Information Overlooked," J. Clin. Monit., vol. 12, No. 5, pp. 365-377, Sep. 1996.

K. H. Shelley, "Photoplethysmography: Beyond the Calculation of Arterial Oxygen Saturation and Heart Rate," Anesth. Analg., vol. 105, No. 6, pp. S31-S36, Dec. 2007.

* cited by examiner

METHODS AND SYSTEMS FOR DETERMINING REGIONAL BLOOD OXYGEN SATURATION

CROSS-REFERENCE TO RELATED APPLICATION

The present disclosure claims priority to U.S. Provisional Application No. 61/942,568, filed Feb. 20, 2014, which is hereby incorporated by reference herein in its entirety.

FIELD OF THE DISCLOSURE

The present disclosure relates to determining blood oxygen saturation in a physiological monitor, and more particularly, relates to determining regional blood oxygen saturation in a regional oximeter or other medical device.

SUMMARY

Methods and systems are provided for determining regional blood oxygen saturation ($rSO_2$) of a subject.

In some embodiments, a system for determining $rSO_2$ of a subject includes processing equipment configured for generating a light drive signal configured to cause one or more light sources to emit a plurality of light signals, wherein the plurality of light signals corresponds to a plurality of wavelengths of light. The processing equipment is further configured for receiving a first plurality of light signals that have been attenuated by a first region of the subject, wherein the first plurality of light signals corresponds to the plurality of wavelengths of light, and receiving a second plurality of light signals that have been attenuated by a second region of the subject, wherein the second plurality of light signals corresponds to the plurality of wavelengths of light. The processing equipment is further configured for determining a plurality of differential absorption values corresponding, respectively, to the plurality of wavelengths of light, wherein each differential absorption value of the plurality of differential absorption values is based on a difference in absorption associated with the first and second regions of the subject for a respective wavelength of light. The processing equipment is further configured for receiving reference sets of absorption data corresponding to different $rSO_2$ values, comparing the plurality of differential absorption values to the reference sets, and determining the $rSO_2$ of the subject based on the comparison.

In some embodiments, a method for determining $rSO_2$ of a subject includes generating a light drive signal configured to cause one or more light sources to emit a plurality of light signals, wherein the plurality of light signals corresponds to a plurality of wavelengths of light. The method further includes receiving a first plurality of light signals that have been attenuated by a first region of the subject, wherein the first plurality of light signals corresponds to the plurality of wavelengths of light, and receiving a second plurality of light signals that have been attenuated by a second region of the subject, wherein the second plurality of light signals corresponds to the plurality of wavelengths of light. The method further includes determining a plurality of differential absorption values corresponding, respectively, to the plurality of wavelengths of light, where each differential absorption value of the plurality of differential absorption values is based on a difference in absorption associated with the first and second regions of the subject for a respective wavelength of light. The method further includes receiving reference sets of absorption data corresponding to different $rSO_2$ values, comparing the plurality of differential absorption values to the reference sets, and determining the $rSO_2$ of the subject based on the comparison.

In some embodiments, a system for determining $rSO_2$ of a subject includes processing equipment configured for generating a light drive signal configured to cause one or more light sources to emit a plurality of light signals, where the plurality of light signals corresponds to three or more wavelengths of light. The processing equipment is further configured for receiving a first plurality of light signals that have been attenuated by a first region of the subject, where the first plurality of light signals corresponds to the three or more wavelengths of light, and receiving a second plurality of light signals that have been attenuated by a second region of the subject, where the second plurality of light signals corresponds to the three or more wavelengths of light. The processing equipment is further configured for determining a plurality of differential absorption values corresponding, respectively, to the plurality of wavelengths of light, wherein each differential absorption value of the plurality of differential absorption values is based on a difference in absorption associated with the first and second regions of the subject for a respective wavelength of light. The processing equipment is further configured for determining two or more $rSO_2$ estimates based on two or more pairs of differential absorption values of the plurality of differential absorption values, where each of the two or more $rSO_2$ estimates is associated with two wavelengths of light, and determining an $rSO_2$ value for the subject based on the two or more rSO2 estimates.

In some embodiments, a method for determining $rSO_2$ of a subject includes generating a light drive signal configured to cause one or more light sources to emit a plurality of light signals, where the plurality of light signals corresponds to three or more wavelengths of light. The method includes receiving a first plurality of light signals that have been attenuated by a first region of the subject, where the first plurality of light signals corresponds to the three or more wavelengths of light, and receiving a second plurality of light signals that have been attenuated by a second region of the subject, where the second plurality of light signals corresponds to the three or more wavelengths of light. The method includes determining a plurality of differential absorption values corresponding, respectively, to the plurality of wavelengths of light, where each differential absorption value of the plurality of differential absorption values is based on a difference in absorption associated with the first and second regions of the subject for a respective wavelength of light. The method includes determining two or more $rSO_2$ estimates based on two or more pairs of differential absorption values of the plurality of differential absorption values, where each of the two or more $rSO_2$ estimates is associated with two wavelengths of light, and determining an $rSO_2$ value for the subject based on the two or more $rSO_2$ estimates.

BRIEF DESCRIPTION OF THE FIGURES

The above and other features of the present disclosure, its nature and various advantages will be more apparent upon consideration of the following detailed description, taken in conjunction with the accompanying drawings in which.

DETAILED DESCRIPTION OF THE FIGURES

Figure 1:
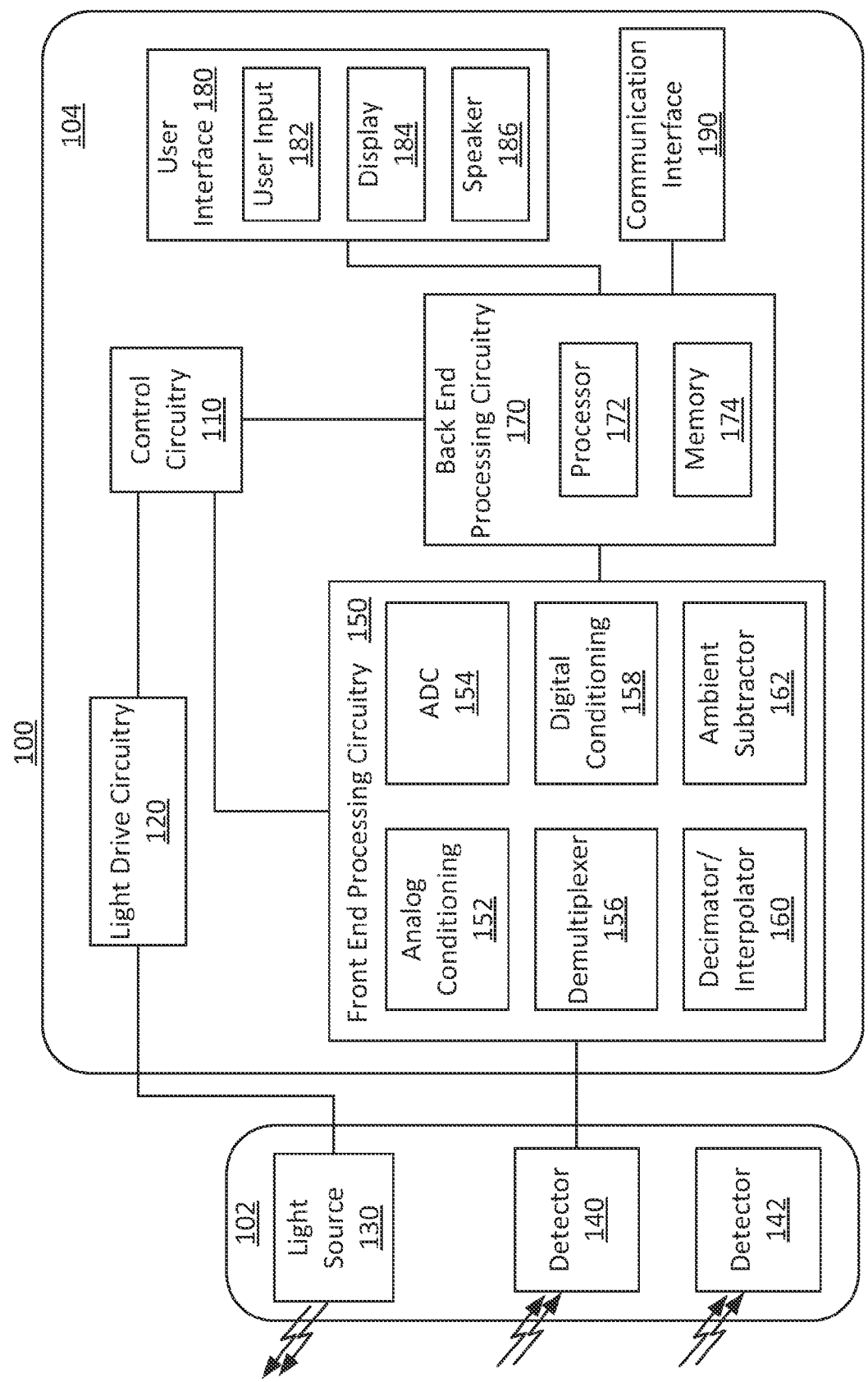
FIG. 1 is a block diagram of an illustrative physiological monitoring system in accordance with some embodiments of the present disclosure.

The present disclosure is directed towards determining an $rSO_2$ value of a subject. Differential absorption values may be determined based on received first light signals and second light signals corresponding to light attenuated by respective first and second regions of the subject. In some embodiments, reference sets (e.g., reference absorption curves) are received, each associated with an $rSO_2$ value and containing expected absorption values. The differential absorption values are compared with the expected absorption values, and an $rSO_2$ value is determined based on the comparison.

In some embodiments, an $rSO_2$ value may also be determined based on multiple $rSO_2$ estimates. The $rSO_2$ estimates are determined based on pairs of the differential absorption values, and two or more $rSO_2$ estimates are combined to determine an $rSO_2$ value of the subject. In some embodiments, confidence measures are computed for the $rSO_2$ values, and an $rSO_2$ value is displayed if the confidence measure indicates a sufficiently high level of confidence in the determined $rSO_2$ value.

The foregoing techniques may be implemented in an oximeter. An oximeter is a medical device that may determine the oxygen saturation of an analyzed tissue. One common type of oximeter is a regional oximeter. A regional oximeter is used to estimate the blood oxygen saturation in a region of a subject's tissue. The regional oximeter may compute a differential absorption value for each of two or more wavelengths of light received at two different locations on the subject's body to estimate the regional blood oxygen saturation of hemoglobin in a region of the subject's tissue. For each wavelength of light, the regional oximeter may compare the amount of light absorbed by the subject's tissue in a first region to the amount of light absorbed by the subject's tissue in a second region to derive the differential absorption values. As opposed to pulse oximetry, which typically examines the oxygen saturation of pulsatile, arterial tissue, regional oximetry examines the oxygen saturation of blood in a region of tissue, which may include blood in the venous, arterial, and capillary systems. For example, a regional oximeter may include a sensor unit configured for placement on a subject's forehead and may be used to estimate the blood oxygen saturation of a region of tissue beneath the sensor unit (e.g., cerebral tissue).

In some embodiments, the oximeter may be a combined oximeter including a regional oximeter and a pulse oximeter. A pulse oximeter is a device for non-invasively measuring the oxygen saturation of a patient's blood (as opposed to measuring oxygen saturation directly by analyzing a blood sample taken from the patient). Pulse oximeters may be included in patient monitoring systems that measure and display various blood flow characteristics including, but not limited to, the oxygen saturation of hemoglobin in arterial blood. Such patient monitoring systems may also measure and display additional physiological parameters, such as a patient's pulse rate, respiration rate, respiration effort, blood pressure, any other suitable physiological parameter, or any combination thereof. Pulse oximetry may be implemented using a photoplethysmograph. Pulse oximeters and other photoplethysmograph devices may also be used to determine other physiological parameter and information as disclosed in: J. Allen, "Photoplethysmography And Its Application In Clinical Physiological Measurement," *Physiol. Meas.*, vol. 28, pp. R1-R39, March 2007; W. B. Murray and P. A. Foster, "The Peripheral Pulse Wave: Information Overlooked," *J. Clin. Monit.*, vol. 12, pp. 365-377, September 1996; and K. H. Shelley, "Photoplethysmography: Beyond the Calculation of Arterial Oxygen Saturation and Heart Rate,"*Anesth. Analg.*, vol. 105, pp. S31-S36, December 2007; all of which are incorporated by reference herein in their entireties.

An oximeter may include a light sensor that is placed at a site on a patient, typically a fingertip, toe, forehead or earlobe, or in the case of a neonate, across a foot or hand. The oximeter may use a light source to pass light through blood perfused tissue and photoelectrically sense the absorption of the light in the tissue. Additional suitable sensor locations include, without limitation, the neck to monitor carotid artery pulsatile flow, the wrist to monitor radial artery pulsatile flow, the inside of a patient's thigh to monitor femoral artery pulsatile flow, the ankle to monitor tibial artery pulsatile flow, around or in front of the ear, locations with strong pulsatile arterial flow, and locations above tissue desired to be analyzed. Suitable sensors for these locations may include sensors that detect reflected light.

The oximeter may measure the intensity of light that is received at the light sensor as a function of time. The oximeter may also include sensors at multiple locations. A signal representing light intensity versus time or a mathematical manipulation of this signal (e.g., a scaled version thereof, a log taken thereof, a scaled version of a log taken thereof, an inverted signal, etc.) may be referred to as the photoplethysmograph (PPG) signal. In addition, the term "PPG signal," as used herein, may also refer to an absorption signal (i.e., representing the amount of light absorbed by the tissue) or any suitable mathematical manipulation thereof. The light intensity or the amount of light absorbed may then be used to calculate any of a number of physiological parameters, including an amount of a blood constituent (e.g., oxyhemoglobin) being measured as well as a pulse rate and when each individual pulse occurs.

In some embodiments, the photonic signal interacting with the tissue is of one or more wavelengths that are attenuated by the blood in an amount representative of the blood constituent concentration. Red and infrared (IR) wavelengths may be used because it has been observed that highly oxygenated blood will absorb relatively less red light and more IR light than blood with a lower oxygen saturation. By comparing the intensities of two wavelengths at different points in the pulse cycle, it is possible to estimate the blood oxygen saturation of hemoglobin in arterial blood.

The system may process data to determine physiological parameters using techniques well known in the art. For example, the system may determine arterial blood oxygen saturation using two wavelengths of light and a ratio-of-ratios calculation. In another example, the system may determine regional blood oxygen saturation using multiple wavelengths of light and a differential absorption technique. The system also may identify pulses and determine pulse amplitude, respiration, blood pressure, other suitable parameters, or any combination thereof, using any suitable calculation techniques. In some embodiments, the system may use information from external sources (e.g., tabulated data, secondary sensor devices) to determine physiological parameters.

In some embodiments, the regional oximeter may include a first sensor located at a first distance from the light source (e.g., the near detector) and a second sensor located at a second farther distance from the light source (e.g., the far detector). In some embodiments, the regional oximeter may include a near detector at a distance of 3 centimeters (cm) and a far detector at a distance of 4 cm from the light source, which may include, for example, one or more emitters. The distance between each detector and the light source affects the mean path length of the detected light and thus the depth of tissue through which the respective received wavelength of light passes. In other words, the light detected by the near detector may pass through shallow, superficial tissue, whereas the light detected by the far detector may pass through additional, deep tissue. In some embodiments, the regional oximeter's light source may include two or more emitters and one or more detectors. For example, a first emitter may be located a short distance from a detector, and the second emitter may be located a longer distance from the detector.

In some embodiments, multiple wavelengths of light may be received at both the near and far detectors, and the intensity of the multiple wavelengths of light may be computed and contrasted at each detector to derive regional blood oxygen saturation. For example, intensity signals for four wavelengths of light may be received at each of the near and far detectors, and the received intensity of each wavelength at the near detector may be subtracted from the received intensity of each wavelength at the far detector. The resulting light signals may be used to compute the regional blood oxygen saturation of a region of deep tissue through which light received at the far detector passed. Because the far detector receives light that passes through deep tissue in addition to the shallow tissue through which the light passes and is received at the near detector, the regional saturation may be computed for just the deep tissue by subtracting out the intensity received by the near detector. For example, a regional oximeter on a subject's forehead may include near and far detectors spaced from the light source such that the near detector receives light that passes through the subject's forehead tissue, including the superficial skin, shallow tissue covering the skull, and the skull, and the far detector receives light that passes through the forehead tissue and brain tissue (i.e., cerebral tissue). In the example, the differences in the light intensities received by the near and far detectors may be used to derive an estimate of the regional blood oxygen saturation of the subject's cerebral tissue (i.e., cerebral blood oxygen saturation).

The following description and accompanying FIGS. 1-11 provide additional details and features of some embodiments of the present disclosure.

FIG. 1 is a block diagram of an illustrative physiological monitoring system 100 in accordance with some embodiments of the present disclosure. System 100 may include a sensor 102 and a monitor 104 for generating and processing physiological signals of a subject. In some embodiments, sensor 102 and monitor 104 may be part of an oximeter.

Sensor 102 of physiological monitoring system 100 may include light source 130, detector 140, and detector 142. Light source 130 may be configured to emit photonic signals having two or more wavelengths of light (e.g., red and IR) into a subject's tissue. For example, light source 130 may include a red light emitting light source and an IR light emitting light source, (e.g., red and IR light emitting diodes (LEDs)), for emitting light into the tissue of a subject to generate physiological signals. In one embodiment, the red wavelength may be between about 600 nm and about 700 nm, and the IR wavelength may be between about 800 nm and about 1000 nm. It will be understood that light source 130 may include any number of light sources with any suitable characteristics. In embodiments where an array of sensors is used in place of single sensor 102, each sensor may be configured to emit a single wavelength. For example, a first sensor may emit only a red light while a second may emit only an IR light. In some embodiments, light source 130 may be configured to emit two or more wavelengths of near-infrared light (e.g., wavelengths between 600 nm and 1000 nm) into a subject's tissue. In some embodiments, light source 130 may be configured to emit four wavelengths of light (e.g., 724 nm, 770 nm, 810 nm, and 850 nm) into a subject's tissue.

It will be understood that, as used herein, the term "light" may refer to energy produced by radiative sources and may include one or more of ultrasound, radio, microwave, millimeter wave, infrared, visible, ultraviolet, gamma ray or X-ray electromagnetic radiation. As used herein, light may also include any wavelength within the radio, microwave, infrared, visible, ultraviolet, or X-ray spectra, and that any suitable wavelength of electromagnetic radiation may be appropriate for use with the present techniques. Detectors 140 and 142 may be chosen to be specifically sensitive to the chosen targeted energy spectrum of light source 130.

In some embodiments, detectors 140 and 142 may be configured to detect the intensity of multiple wavelengths of near-infrared light. In some embodiments, detectors 140 and 142 may be configured to detect the intensity of light at the red and IR wavelengths. In some embodiments, an array of sensors may be used and each sensor in the array may be configured to detect an intensity of a single wavelength. In operation, light may enter detector 140 after passing through the subject's tissue, including skin, bone, and other shallow tissue (e.g., non-cerebral tissue and shallow cerebral tissue).

Light may enter detector 142 after passing through the subject's tissue, including skin, bone, other shallow tissue (e.g., non-cerebral tissue and shallow cerebral tissue), and deep tissue (e.g., deep cerebral tissue). Detectors 140 and 142 may convert the intensity of the received light into an electrical signal. The light intensity may be directly related to the absorbance and/or reflectance of light in the tissue. That is, when more light at a certain wavelength is absorbed or reflected, less light of that wavelength is received from the tissue by detectors 140 and 142. After converting the received light to an electrical signal, detectors 140 and 142 may send the detection signals to monitor 104, where the detection signals may be processed and physiological parameters may be determined (e.g., based on the absorption of the red and IR wavelengths in the subject's tissue at both detectors). In some embodiments, one or more of the detection signals may be preprocessed by sensor 102 before being transmitted to monitor 104.

In the embodiment shown, monitor 104 includes control circuitry 110, light drive circuitry 120, front end processing circuitry 150, back end processing circuitry 170, user interface 180, and communication interface 190. Monitor 104 may be communicatively coupled to sensor 102.

Control circuitry 110 may be coupled to light drive circuitry 120, front end processing circuitry 150, and back end processing circuitry 170, and may be configured to control the operation of these components. In some embodiments, control circuitry 110 may be configured to provide timing control signals to coordinate their operation. For example, light drive circuitry 120 may generate one or more light drive signals, which may be used to turn on and off the light source 130, based on the timing control signals. The front end processing circuitry 150 may use the timing control signals to operate synchronously with light drive circuitry 120. For example, front end processing circuitry 150 may synchronize the operation of an analog-to-digital converter and a demultiplexer with the light drive signal based on the timing control signals. In addition, the back end processing circuitry 170 may use the timing control signals to coordinate its operation with front end processing circuitry 150.

Light drive circuitry 120, as discussed above, may be configured to generate a light drive signal that is provided to light source 130 of sensor 102. The light drive signal may, for example, control the intensity of light source 130 and the timing of when light source 130 is turned on and off. In some embodiments, light drive circuitry 130 provides one or more light drive signals to light source 130. Where light source 130 is configured to emit two or more wavelengths of light, the light drive signal may be configured to control the operation of each wavelength of light. The light drive signal may comprise a single signal or may comprise multiple signals (e.g., one signal for each wavelength of light).

Figure 2A:
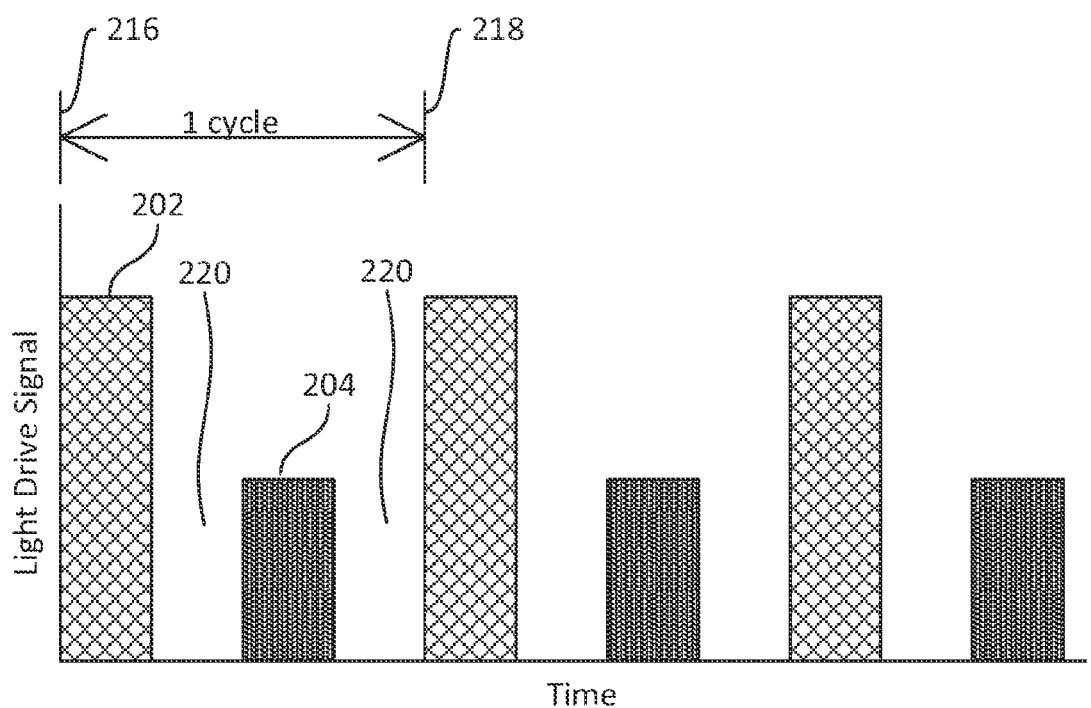
FIG. 2A shows an illustrative plot of a light drive signal in accordance with some embodiments of the present disclosure.

FIG. 2A shows an illustrative plot of a light drive signal including red light drive pulse 202 and IR light drive pulse 204 in accordance with some embodiments of the present disclosure. In the illustrated embodiment, light drive pulses 202 and 204 are shown as square waves. It will be understood that square waves are presented merely as an illustrative example, not by way of limitation, and that these pulses may include any other suitable signal, for example, shaped pulse waveforms, rather than a square waves. The shape of the pulses may be generated by a digital signal generator, digital filters, analog filters, any other suitable equipment, or any combination thereof. For example, light drive pulses 202 and 204 may be generated by light drive circuitry 120 under the control of control circuitry 110. As used herein, drive pulses may refer to the high and low states of a pulse, switching power or other components on and off, high and low output states, high and low values within a continuous modulation, other suitable relatively distinct states, or any combination thereof. The light drive signal may be provided to light source 130, including red light drive pulse 202 and IR light drive pulse 204 to drive red and IR light emitters, respectively, within light source 130.

Red light drive pulse 202 may have a higher amplitude than IR light drive 204 since red LEDs may be less efficient than IR LEDs at converting electrical energy into light energy. In some embodiments, the output levels may be equal, may be adjusted for nonlinearity of emitters, may be modulated in any other suitable technique, or any combination thereof. Additionally, red light may be absorbed and scattered more than IR light when passing through perfused tissue.

When the red and IR light sources are driven in this manner they emit pulses of light at their respective wavelengths into the tissue of a subject in order generate physiological signals that physiological monitoring system 100 may process to calculate physiological parameters. It will be understood that the light drive amplitudes of FIG. 2A are merely exemplary and that any suitable amplitudes or combination of amplitudes may be used, and may be based on the light sources, the subject tissue, the determined physiological parameter, modulation techniques, power sources, any other suitable criteria, or any combination thereof. It will also be understood that in systems that use more than two wavelengths of light, additional light drive pulses may be included in the light drive signal. For example, when four wavelengths of light are used, four light drive pulses, one for each wavelength of light, may be included in the light drive signal.

The light drive signal of FIG. 2A may also include "off" periods 220 between the red and IR light drive pulse. "Off" periods 220 are periods during which no drive current may be applied to light source 130. "Off" periods 220 may be provided, for example, to prevent overlap of the emitted light, since light source 130 may require time to turn completely on and completely off. The period from time 216 to time 218 may be referred to as a drive cycle, which includes four segments: a red light drive pulse 202, followed by an "off" period 220, followed by an IR light drive pulse 204, and followed by an "off" period 220. After time 218, the drive cycle may be repeated (e.g., as long as a light drive signal is provided to light source 130). It will be understood that the starting point of the drive cycle is merely illustrative and that the drive cycle can start at any location within FIG. 2A, provided the cycle spans two drive pulses and two "off" periods. Thus, each red light drive pulse 202 and each IR light drive pulse 204 may be understood to be surrounded by two "off" periods 220. "Off" periods may also be referred to as dark periods, in that the emitters are dark or returning to dark during that period. It will be understood that the particular square pulses illustrated in FIG. 2A are merely exemplary and that any suitable light drive scheme is possible. For example, light drive schemes may include shaped pulses, sinusoidal modulations, time division multiplexing other than as shown, frequency division multiplexing, phase division multiplexing, any other suitable light drive scheme, or any combination thereof.

Referring back to FIG. 1, front end processing circuitry 150 may receive detection signals from detectors 140 and 142 and provide two or more processed signals to back end processing circuitry 170. The term "detection signals," as used herein, may refer to any of the signals generated within front end processing circuitry 150 as it processes the output signal of detectors 140 and 142. Front end processing circuitry 150 may perform various analog and digital processing of the detector signals. One suitable detector signal that may be received by front end processing circuitry 150 is shown in FIG. 2B.

Figure 2B:
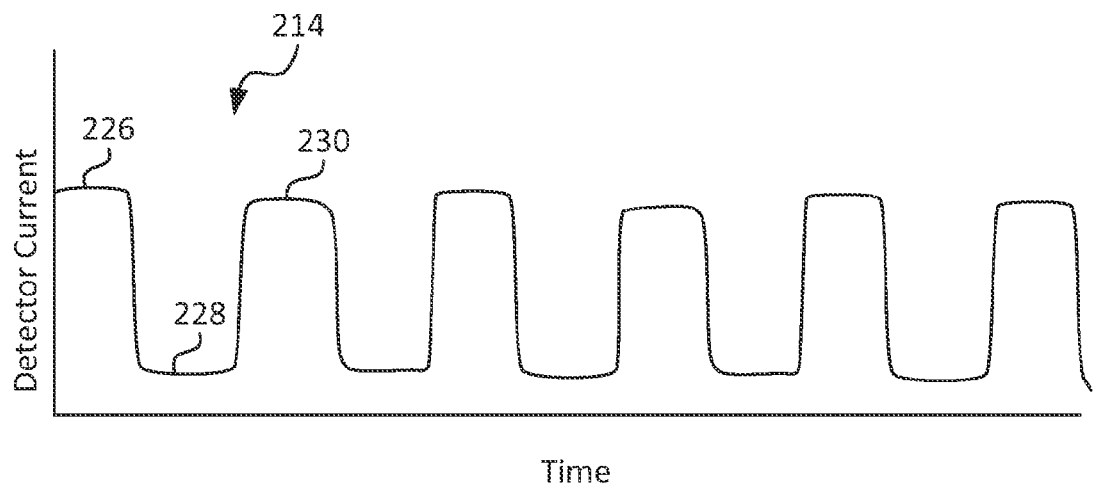
FIG. 2B shows an illustrative plot of a detector signal that may be generated by a sensor in accordance with some embodiments of the present disclosure.

FIG. 2B shows an illustrative plot of detector current waveform 214 that may be generated by a sensor in accordance with some embodiments of the present disclosure. The peaks of detector current waveform 214 may represent current signals provided by a detector, such as detectors 140 and 142 of FIG. 1, when light is being emitted from a light source. The amplitude of detector current waveform 214 may be proportional to the light incident upon the detector. The peaks of detector current waveform 214 may be synchronous with drive pulses driving one or more emitters of a light source, such as light source 130 of FIG. 1. For example, detector current peak 226 may be generated in response to a light source being driven by red light drive pulse 202 of FIG. 2A, and peak 230 may be generated in response to a light source being driven by IR light drive pulse 204. Valley 228 of detector current waveform 214 may be synchronous with periods of time during which no light is being emitted by the light source, or the light source is returning to dark, such as "off" period 220. While no light is being emitted by a light source during the valleys, detector current waveform 214 may not fall all of the way to zero.

It will be understood that detector current waveform 214 may be an at least partially idealized representation of a detector signal, assuming perfect light signal generation, transmission, and detection. It will be understood that an actual detector current will include amplitude fluctuations, frequency deviations, droop, overshoot, undershoot, rise time deviations, fall time deviations, other deviations from the ideal, or any combination thereof. It will be understood that the system may shape the drive pulses shown in FIG. 2A in order to make the detector current as similar as possible to idealized detector current waveform 214.

Referring back to FIG. 1, front end processing circuitry 150, which may receive detection signals, such as detector current waveform 214, may include analog conditioning 152, analog-to-digital converter (ADC) 154, demultiplexer 156, digital conditioning 158, decimator/interpolator 160, and ambient subtractor 162.

Analog conditioning 152 may perform any suitable analog conditioning of the detector signals. The conditioning performed may include any type of filtering (e.g., low pass, high pass, band pass, notch, or any other suitable filtering), amplifying, performing an operation on the received signal (e.g., taking a derivative, averaging), performing any other suitable signal conditioning (e.g., converting a current signal to a voltage signal), or any combination thereof.

The conditioned analog signals may be processed by analog-to-digital converter 154, which may convert the conditioned analog signals into digital signals. Analog-to-digital converter 154 may operate under the control of control circuitry 110. Analog-to-digital converter 154 may use timing control signals from control circuitry 110 to determine when to sample the analog signal. Analog-to-digital converter 154 may be any suitable type of analog-to-digital converter of sufficient resolution to enable a physiological monitor to accurately determine physiological parameters. In some embodiments, analog-to-digital converter 154 may be a two channel analog-to-digital converter, where each channel is used for a respective detector waveform.

Demultiplexer 156 may operate on the analog or digital form of the detector signals to separate out different components of the signals. For example, detector current waveform 214 of FIG. 2B includes a red component corresponding to peak 226, an IR component corresponding to peak 230, and at least one ambient component corresponding to valley 228. Demultiplexer 156 may operate on detector current waveform 214 of FIG. 2B to generate a red signal, an IR signal, a first ambient signal (e.g., corresponding to the ambient component corresponding to valley 228 that occurs immediately after the peak 226), and a second ambient signal (e.g., corresponding to the ambient component corresponding to the valley that occurs immediately after the IR component 230). Demultiplexer 156 may operate under the control of control circuitry 110. For example, demultiplexer 156 may use timing control signals from control circuitry 110 to identify and separate out the different components of the detector signals.

Digital conditioning 158 may perform any suitable digital conditioning of the detector signals. Digital conditioning 158 may include any type of digital filtering of the signal (e.g., low pass, high pass, band pass, notch, averaging, or any other suitable filtering), amplifying, performing an operation on the signal, performing any other suitable digital conditioning, or any combination thereof.

Decimator/interpolator 160 may decrease the number of samples in the digital detector signals. For example, decimator/interpolator 160 may decrease the number of samples by removing samples from the detector signals or replacing samples with a smaller number of samples. The decimation or interpolation operation may include or be followed by filtering to smooth the output signal.

Ambient subtractor 162 may operate on the digital signal. In some embodiments, ambient subtractor 162 may remove dark or ambient contributions to the received signal.

The components of front end processing circuitry 150 are merely illustrative and any suitable components and combinations of components may be used to perform the front end processing operations.

The front end processing circuitry 150 may be configured to take advantage of the full dynamic range of analog-to-digital converter 154. This may be achieved by applying gain to the detection signals by analog conditioning 152 to map the expected range of the detection signals to the full or close to full output range of analog-to-digital converter 154. The output value of analog-to-digital converter 154, as a function of the total analog gain applied to each of the detection signals, may be given as:

ADC Value=Total Analog Gain×[Ambient Light+ LED Light]

Ideally, when ambient light is zero and when the light source is off, the analog-to-digital converter 154 will read just above the minimum input value. When the light source is on, the total analog gain may be set such that the output of analog-to-digital converter 154 may read close to the full scale of analog-to-digital converter 154 without saturating. This may allow the full dynamic range of analog-to-digital converter 154 to be used for representing the detection signals, thereby increasing the resolution of the converted signal. In some embodiments, the total analog gain may be reduced by a small amount so that small changes in the light levels incident on the detectors do not cause saturation of analog-to-digital converter 154.

However, if the contribution of ambient light is large relative to the contribution of light from a light source, the total analog gain applied to the detection current may need to be reduced to avoid saturating analog-to-digital converter 154. When the analog gain is reduced, the portion of the signal corresponding to the light source may map to a smaller number of analog-to-digital conversion bits. Thus, more ambient light noise in the input of analog-to-digital converter 154 may result in fewer bits of resolution for the portion of the signal from the light source. This may have a detrimental effect on the signal-to-noise ratio of the detection signals. Accordingly, passive or active filtering or signal modification techniques may be employed to reduce the effect of ambient light on the detection signals that are applied to analog-to-digital converter 154, and thereby reduce the contribution of the noise component to the converted digital signal.

Back end processing circuitry 170 may include processor 172 and memory 174. Processor 172 may be adapted to execute software, which may include an operating system and one or more applications, as part of performing the functions described herein. Processor 172 may receive and further process physiological signals received from front end processing circuitry 150. For example, processor 172 may determine one or more physiological parameters based on the received physiological signals. Processor 172 may include an assembly of analog or digital electronic components. Processor 172 may calculate physiological information. For example, processor 172 may compute one or more of regional oxygen saturation, blood oxygen saturation (e.g., arterial, venous, or both), pulse rate, respiration rate, respiration effort, blood pressure, hemoglobin concentration (e.g., oxygenated, deoxygenated, and/or total), any other suitable physiological parameters, or any combination thereof. Processor 172 may perform any suitable signal processing of a signal, such as any suitable band-pass filtering, adaptive filtering, closed-loop filtering, any other suitable filtering, and/or any combination thereof. Processor 172 may also receive input signals from additional sources not shown. For example, processor 172 may receive an input signal containing information about treatments provided to the subject from user interface 180. Additional input signals may be used by processor 172 in any of the calculations or operations it performs in accordance with back end processing circuitry 170 or monitor 104.

Memory 174 may include any suitable computer-readable media capable of storing information that can be interpreted by processor 172. In some embodiments, memory 174 may store reference absorption curves, reference sets, calculated values, such as blood oxygen saturation, pulse rate, blood pressure, fiducial point locations or characteristics, initialization parameters, any other calculated values, or any combination thereof, in a memory device for later retrieval. This information may be data or may take the form of computer-executable instructions, such as software applications, that cause the microprocessor to perform certain functions and/or computer-implemented methods. Depending on the embodiment, such computer-readable media may include computer storage media and communication media. Computer storage media may include volatile and non-volatile, removable and non-removable media implemented in any method or technology for storage of information such as computer-readable instructions, data structures, program modules or other data. Computer storage media may include, but is not limited to, RAM, ROM, EPROM, EEPROM, flash memory or other solid state memory technology, CD-ROM, DVD, or other optical storage, magnetic cassettes, magnetic tape, magnetic disk storage or other magnetic storage devices, or any other medium which can be used to store the desired information and which can be accessed by components of the system. Back end processing circuitry 170 may be communicatively coupled with user interface 180 and communication interface 190.

User interface 180 may include user input 182, display 184, and speaker 186. User interface 180 may include, for example, any suitable device such as one or more medical devices (e.g., a medical monitor that displays various physiological parameters, a medical alarm, or any other suitable medical device that either displays physiological parameters or uses the output of back end processing 170 as an input), one or more display devices (e.g., monitor, personal digital assistant (PDA), mobile phone, tablet computer, any other suitable display device, or any combination thereof), one or more audio devices, one or more memory devices (e.g., hard disk drive, flash memory, RAM, optical disk, any other suitable memory device, or any combination thereof), one or more printing devices, any other suitable output device, or any combination thereof.

User input 182 may include any type of user input device such as a keyboard, a mouse, a touch screen, buttons, switches, a microphone, a joy stick, a touch pad, or any other suitable input device. The inputs received by user input 182 can include information about the subject, such as age, weight, height, diagnosis, medications, treatments, and so forth.

In an embodiment, the subject may be a medical patient and display 184 may exhibit a list of values which may generally apply to the subject, such as, for example, age ranges or medication families, which the user may select using user input 182. Additionally, display 184 may display, for example, one or more estimates of a subject's regional oxygen saturation generated by monitor 104 (referred to as an "$rSO_2$" measurement), an estimate of a subject's blood oxygen saturation generated by monitor 104 (referred to as an "$SpO_2$" measurement), pulse rate information, respiration rate information, blood pressure, any other parameters, and any combination thereof. Display 184 may include any type of display such as a cathode ray tube display, a flat panel display such a liquid crystal display or plasma display, or any other suitable display device. Speaker 186 within user interface 180 may provide an audible sound that may be used in various embodiments, such as for example, sounding an audible alarm in the event that a patient's physiological parameters are not within a predefined normal range.

Communication interface 190 may enable monitor 104 to exchange information with external devices. Communications interface 190 may include any suitable hardware, software, or both, which may allow monitor 104 to communicate with electronic circuitry, a device, a network, a server or other workstations, a display, or any combination thereof. Communications interface 190 may include one or more receivers, transmitters, transceivers, antennas, plug-in connectors, ports, communications buses, communications protocols, device identification protocols, any other suitable hardware or software, or any combination thereof. Communications interface 190 may be configured to allow wired communication (e.g., using USB, RS-232, Ethernet, or other standards), wireless communication (e.g., using WiFi, IR, WiMax, BLUETOOTH, USB, or other standards), or both. For example, communications interface 190 may be configured using a universal serial bus (USB) protocol (e.g., USB 2.0, USB 3.0), and may be configured to couple to other devices (e.g., remote memory devices storing templates) using a four-pin USB standard Type-A connector (e.g., plug and/or socket) and cable. In some embodiments, communications interface 190 may include an internal bus such as, for example, one or more slots for insertion of expansion cards.

It will be understood that the components of physiological monitoring system 100 that are shown and described as separate components are shown and described as such for illustrative purposes only. In some embodiments the functionality of some of the components may be combined in a single component. For example, the functionality of front end processing circuitry 150 and back end processing circuitry 170 may be combined in a single processor system. Additionally, in some embodiments the functionality of some of the components of monitor 104 shown and described herein may be divided over multiple components. For example, some or all of the functionality of control circuitry 110 may be performed in front end processing circuitry 150, in back end processing circuitry 170, or both. In other embodiments, the functionality of one or more of the components may be performed in a different order or may not be required. In an embodiment, all of the components of physiological monitoring system 100 can be realized in processor circuitry.

Figure 3:
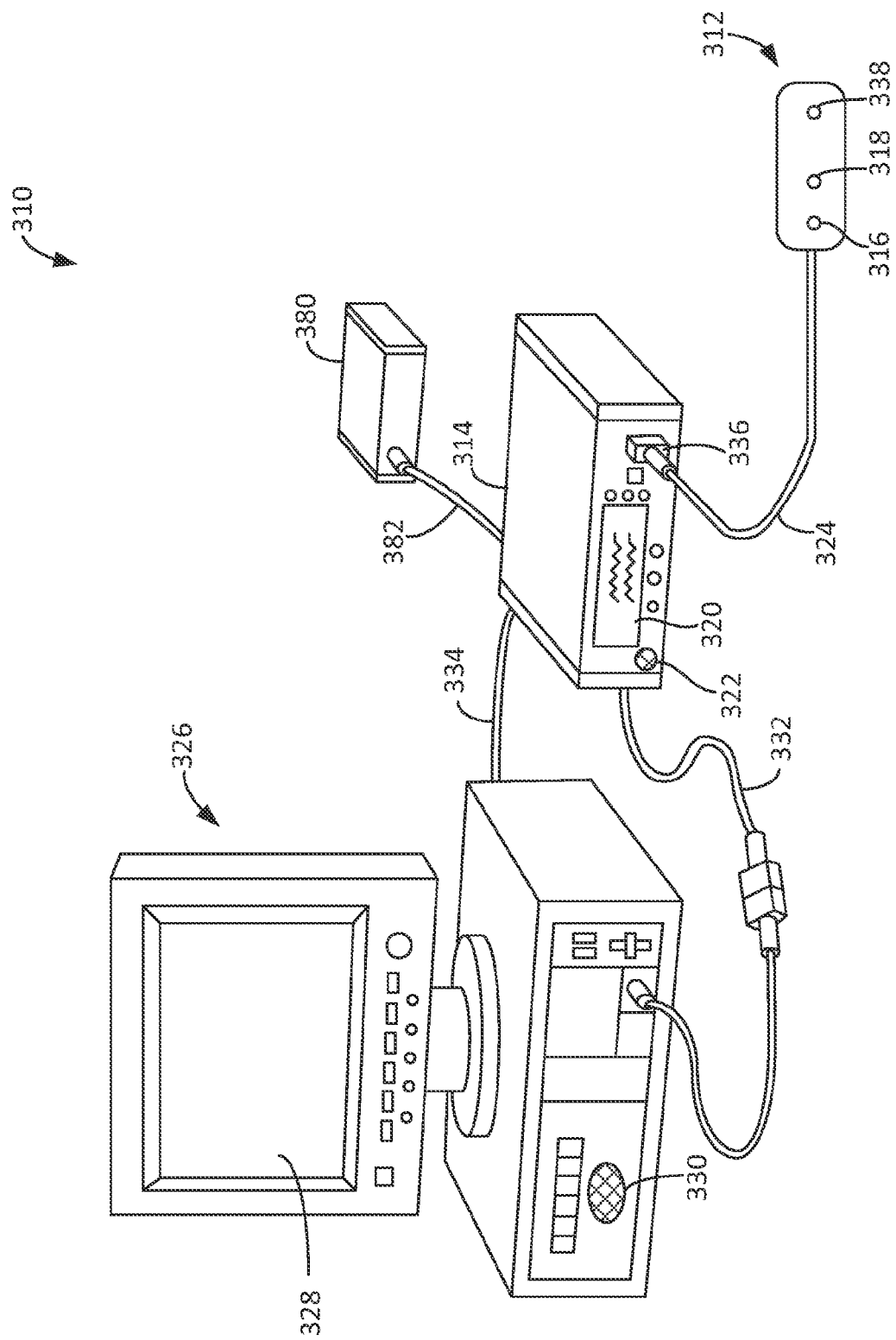
FIG. 3 is a perspective view of an illustrative physiological monitoring system in accordance with some embodiments of the present disclosure.

FIG. 3 is a perspective view of an illustrative physiological monitoring system 310 in accordance with some embodiments of the present disclosure. In some embodiments, one or more components of physiological monitoring system 310 may include one or more components of physiological monitoring system 100 of FIG. 1. Physiological monitoring system 310 may include sensor unit 312 and monitor 314. In some embodiments, sensor unit 312 may be part of an oximeter. Sensor unit 312 may include one or more light source 316 for emitting light at one or more wavelengths into a subject's tissue. Detectors 318 and 338 may also be provided in sensor unit 312 for detecting the light that is reflected by or has traveled through the subject's tissue. Any suitable configuration of light source 316 and detectors 318 and 338 may be used. In some embodiments, sensor unit 312 may include multiple light sources and detectors, which may be spaced apart. In some embodiments, detector 318 (i.e., the near detector) may be positioned at a location closer to light source 316 than detector 338 (i.e., the far detector). Physiological monitoring system 310 may also include one or more additional sensor units (not shown) that may, for example, take the form of any of the embodiments described herein with reference to sensor unit 312. An additional sensor unit may be the same type of sensor unit as sensor unit 312, or a different sensor unit type than sensor unit 312 (e.g., a photoacoustic sensor). Multiple sensor units may be capable of being positioned at two different locations on a subject's body.

In some embodiments, sensor unit 312 may be connected to monitor 314 as shown. Sensor unit 312 may be powered by an internal power source, e.g., a battery (not shown). Sensor unit 312 may draw power from monitor 314. In another embodiment, the sensor may be wirelessly connected (not shown) to monitor 314. Monitor 314 may be configured to calculate physiological parameters based at least in part on data relating to light emission and acoustic detection received from one or more sensor units such as sensor unit 312. For example, monitor 314 may be configured to determine regional oxygen saturation, pulse rate, respiration rate, respiration effort, blood pressure, blood oxygen saturation (e.g., arterial, venous, or both), hemoglobin concentration (e.g., oxygenated, deoxygenated, and/or total), any other suitable physiological parameters, or any combination thereof. In some embodiments, calculations may be performed on the sensor units or an intermediate device and the result of the calculations may be passed to monitor 314. Further, monitor 314 may include display 320 configured to display the physiological parameters or other information about the system. In the embodiment shown, monitor 314 may also include a speaker 322 to provide an audible sound that may be used in various other embodiments, such as for example, sounding an audible alarm in the event that a subject's physiological parameters are not within a predefined normal range. In some embodiments, physiological monitoring system 310 may include a stand-alone monitor in communication with the monitor 314 via a cable or a wireless network link. In some embodiments, monitor 314 may be implemented as monitor 104 of FIG. 1.

In some embodiments, sensor unit 312 may be communicatively coupled to monitor 314 via a cable 324 at port 336. Cable 324 may include electronic conductors (e.g., wires for transmitting electronic signals from detectors 318 and 338), optical fibers (e.g., multi-mode or single-mode fibers for transmitting emitted light from light source 316), any other suitable components, any suitable insulation or sheathing, or any combination thereof. In some embodiments, a wireless transmission device (not shown) or the like may be used instead of or in addition to cable 324. Monitor 314 may include a sensor interface configured to receive physiological signals from sensor unit 312, provide signals and power to sensor unit 312, or otherwise communicate with sensor unit 312. The sensor interface may include any suitable hardware, software, or both, which may allow communication between monitor 314 and sensor unit 312.

In some embodiments, physiological monitoring system 310 may include calibration device 380. Calibration device 380, which may be powered by monitor 314, a battery, or by a conventional power source such as a wall outlet, may include any suitable calibration device. Calibration device 380 may be communicatively coupled to monitor 314 via communicative coupling 382, and/or may communicate wirelessly (not shown). In some embodiments, calibration device 380 is completely integrated within monitor 314. In some embodiments, calibration device 380 may include a manual input device (not shown) used by an operator to manually input reference signal measurements obtained from some other source (e.g., an external invasive or non-invasive physiological measurement system).

In the illustrated embodiment, physiological monitoring system 310 includes a multi-parameter physiological monitor 326. The monitor 326 may include a cathode ray tube display, a flat panel display (as shown) such as a liquid crystal display (LCD) or a plasma display, or may include any other type of monitor now known or later developed. Multi-parameter physiological monitor 326 may be configured to calculate physiological parameters and to provide a display 328 for information from monitor 314 and from other medical monitoring devices or systems (not shown). For example, multi-parameter physiological monitor 326 may be configured to display an estimate of a subject's blood oxygen saturation and hemoglobin concentration generated by monitor 314. Multi-parameter physiological monitor 326 may include a speaker 330.

Monitor 314 may be communicatively coupled to multi-parameter physiological monitor 326 via a cable 332 or 334 that is coupled to a sensor input port or a digital communications port, respectively and/or may communicate wirelessly (not shown). In addition, monitor 314 and/or multi-parameter physiological monitor 326 may be coupled to a network to enable the sharing of information with servers or other workstations (not shown). Monitor 314 may be powered by a battery (not shown) or by a conventional power source such as a wall outlet.

In some embodiments, any of the processing components and/or circuits, or portions thereof, of FIGS. 1 and 3, including sensors 102 and 312 and monitors 104, 314, and 326 may be referred to collectively as processing equipment. For example, processing equipment may be configured to amplify, filter, sample and digitize an input signal from sensor 102 or 312 (e.g., using an analog-to-digital converter), calculate physiological information and metrics from the digitized signal, and display a trace of the physiological information. In some embodiments, all or some of the components of the processing equipment may be referred to as a processing module. In some embodiments, the processing equipment may be part of a regional oximetry system, and sensors 102 and 312 of FIGS. 1 and 3 may correspond to regional oximeter sensor unit 400 of FIG. 4, described below.

Figure 4:
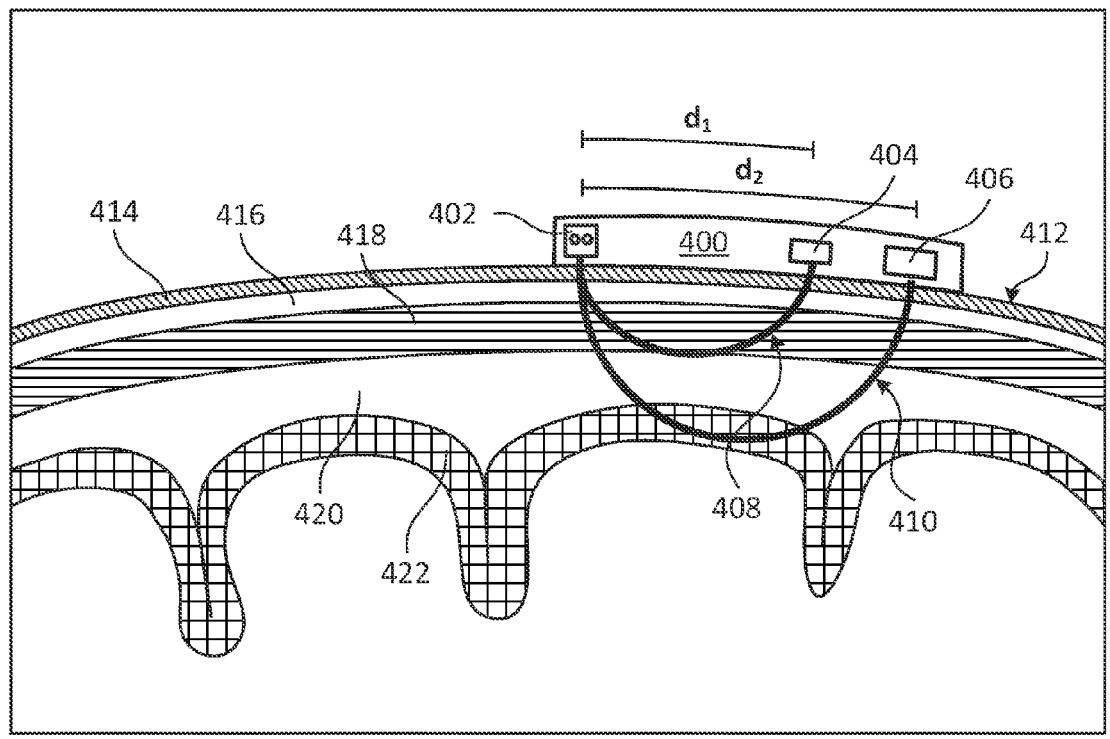
FIG. 4 is a cross-sectional view of an illustrative regional oximeter sensor unit applied to a subject's cranium in accordance with some embodiments of the present disclosure.

FIG. 4 is a cross-sectional view of an illustrative regional oximeter sensor unit 400 applied to a subject's cranium in accordance with some embodiments of the present disclosure. Regional oximeter sensor unit 400 includes light source 402, near detector 404, and far detector 406 and is shown as positioned on a subject's forehead 412. In the illustrated embodiment, light source 402 generates a light signal, which is shown traveling first and second mean path lengths 408 and 410 to respective near and far detectors 404 and 406. As shown, first and second mean path lengths 408 and 410 traverse the subject's cranial structure at different depths. The subject's cranial structure includes outer skin 414, shallow tissue 416, and cranial bone 416 (i.e., the frontal shell of the skull). Beneath cranial bone 416 is Dura Mater 420 and cerebral tissue 422.

In some embodiments, light source 402 of sensor unit 400 may include one or more emitters for emitting light into the tissue of a subject to generate physiological signals. Detectors 404 and 406 may be positioned on sensor unit 400 such that near detector 404 is located at a distance $d_1$ from light source 402 and far detector 406 is located at a distance $d_2$ from light source 402. As shown, distance $d_1$ is shorter than distance $d_2$, and it will be understood that any suitable distances $d_1$ and $d_2$ may be used such that mean path length 408 of light detected by near detector 404 is shorter than the mean path length 410 of far detector 406. Near detector 404 may receive the light signal after it has traveled first mean path length 408, and far detector 406 may receive the light signal after it has traveled second mean path length 410. First mean path length 408 may traverse the subject's outer skin 414, shallow tissue 416, cranial bone 416, and Dura Mater 420. In some embodiments, first mean path length 408 may also traverse shallow cerebral tissue 422. Second mean path length 410 may traverse the subject's outer skin 414, shallow tissue 416, cranial bone 416, Dura Mater 420, and cerebral tissue 422.

In some embodiments, regional oximeter sensor unit 400 may be part of a regional oximetry system for determining the amount of light absorbed by a region of a subject's tissue. As described in detail above, for each wavelength of light, an absorption value may be determined based on the amount of light received at near detector 404, and an absorption value may be determined based on the amount of light received at far detector 406. For each wavelength of light, a differential absorption value may be computed based on the difference between the absorption values determined for near detector 404 and far detector 406. The differential absorption values may be representative of the amount of light absorbed by cerebral tissue 422 at each wavelength. In some embodiments, the differential absorption values $\Delta A_{\lambda,i}$ may be given by:

$$\Delta A_{\lambda,i} = A_{\lambda,i,shall} - A_{\lambda,i,deep}, \quad (1)$$

where $\Delta A_{\lambda,i,deep}$ denotes the attenuation of light between light source 402 and far detector 406, $A_{\lambda,i,shall}$ denotes the attenuation of light between light source 402 and near detector 404, and the $\lambda_i$ denotes a wavelength of light. In some embodiments, a detected light signal may be normalized, for example, based on the amount of light emitted by light source 402, characteristics of the detector, system gains, other suitable properties of the system, and/or empirical data. The processing equipment may determine the differential absorption values $\Delta A_{\lambda,i}$ based on eq. 1, using normalized values for the attenuation of light between light source 402 and far detector 406 and the attenuation of light between light source 402 and near detector 404.

Figure 5:
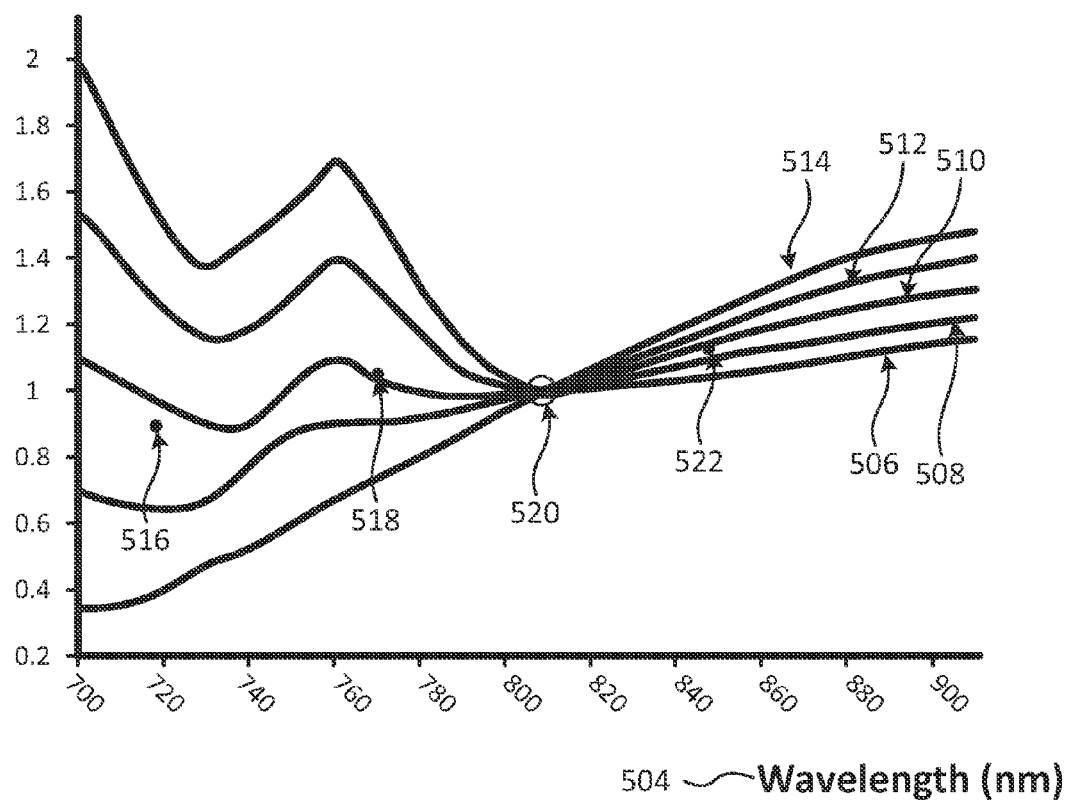
FIG. 5 shows an illustrative plot of absorption values in accordance with some embodiments of the present disclosure.

Light in the near-infrared spectrum (i.e., 600 nm to 1000 nm) is absorbed differently by the $HbO_2$ and $Hb$ in a subject's blood, with the exception of light at the isosbestic point, (i.e., approximately 808 nm), where $HbO_2$ and $Hb$ exhibit the same absorptivity. For example, $HbO_2$ and $Hb$ exhibit different optical absorption spectra when radiated with 640 nm (RED) and 940 nm (IR) light. Thus, assuming absorption may be attributed to $HbO_2$ and $Hb$, each possible $rSO_2$ value corresponds to a unique set of absorption values (i.e., absorption/wavelength of light). In some embodiments, each possible $rSO_2$ value may correspond to a reference set of differential absorption values (i.e., absorption/wavelength of light). These reference sets of absorption data may be represented as reference absorption curves (i.e., plotted as absorption versus wavelengths of light). Exemplary reference absorption curves are shown in FIG. 5, described below. For example, a subject with an $rSO_2$ value of 20 may be expected to exhibit certain expected absorption values for a spectrum of wavelengths of light, and these expected absorption values may be represented as a reference absorption curve associated with an $rSO_2$ value of 20. The reference absorption curve for an $rSO_2$ value of 20 would differ, however, from the reference absorption curve for an $rSO_2$ value of 80.

FIG. 5 shows an illustrative plot 500 of absorption data in accordance with some embodiments of the present disclosure. Vertical axis 502 of plot 500 corresponds to normalized absorption values, indicative of the amount of light absorbed by a subject's tissue. Horizontal axis 504 of plot 500 corresponds to wavelengths of light in the near-infrared spectrum, expressed in nanometers (nm). Plot 500 depicts five reference absorption curves, 506, 508, 510, 512, and 514, each associated with a different $rSO_2$ value.

In some embodiments, a reference absorption curve $A(rSO_2)$ may be generated based on $$A(rSO_2) = rSO_2 \cdot \mu HbO_{2\lambda} + (1 - rSO_2) \cdot \mu Hb_\lambda \quad (2)$$

where $\mu HbO_{2\lambda}$ denotes the absorption coefficient for oxygenated hemoglobin for wavelength $\lambda$, and $\mu Hb_\lambda$ denotes the absorption coefficient for deoxygenated hemoglobin for wavelength $\lambda$. The reference absorption curves may also be derived from empirical calibration studies on human subjects. The monitor may have multiple reference curves depending on the monitoring site, for example one set of empirical curves for cerebral sites and another set for somatic sites (e.g., calf, spine, forearm, etc.). Multiple curves may also exist dependent upon the subject's age and/or weight. Although we expect hemoglobin absorption curves to be the similar at all sites and body types, baseline tissue scattering properties at certain sites may alter the shape of a "nominal absorption curve."

In some embodiments, the processing equipment may determine a subject's $rSO_2$ value based on the reference sets of differential absorption values. In some embodiments, the reference sets may be represented as reference absorption curves 506, 508, 510, 512, and 514. As discussed above, a unique reference set and corresponding reference curve may be generated for each possible $rSO_2$ value. In the illustrated example, reference absorption curve 506 may correspond to a reference set of absorption data for an $rSO_2$ value of 100. Reference absorption curve 508 may correspond to a reference set of absorption data for an $rSO_2$ value of 80. Reference absorption curve 510 may correspond to a reference set of absorption data for an $rSO_2$ value of 60. Reference absorption curve 512 may correspond to a reference set of absorption data for an $rSO_2$ value of 40. Reference absorption curve 514 may correspond to a reference set of absorption data for an $rSO_2$ value of 20. It will be understood that the reference absorption curves are not limited to the five reference curves presented and may correspond to any other absorption curves computed for particular $rSO_2$ values. In some embodiments, the processing equipment may compute multiple differential absorption values for a subject, as discussed above. For example, the differential absorption values may correspond to points 516, 518, 520, and 522, which represent the amounts of absorption determined, respectively, for light signals corresponding to wavelengths of approximately 724 nm, 770 nm, 810 nm, and 850 nm. The processing equipment may compare the differential absorption values to reference sets of absorption data (e.g., reference absorption curves 506, 508, 510, 512, and 514) and determine an $rSO_2$ value based on the comparison. In some embodiments, the processing equipment may determine a best fit reference set by comparing the differential absorption values to reference sets. For example, the processing equipment may compare points 516, 518, 520, and 522 to reference absorption curves 506, 508, 510, 512, and 514 and determine that reference absorption curve 510 is the best fit reference absorption curve. The processing equipment may determine an $rSO_2$ value of 60 for the subject based on the best fit reference absorption curve 510, because reference absorption curve 510 corresponds to an $rSO_2$ value of 60, as described above. Determining an $rSO_2$ value using reference sets of absorption data is discussed in further detail below, with reference to FIGS. 6-8.

Figure 6:
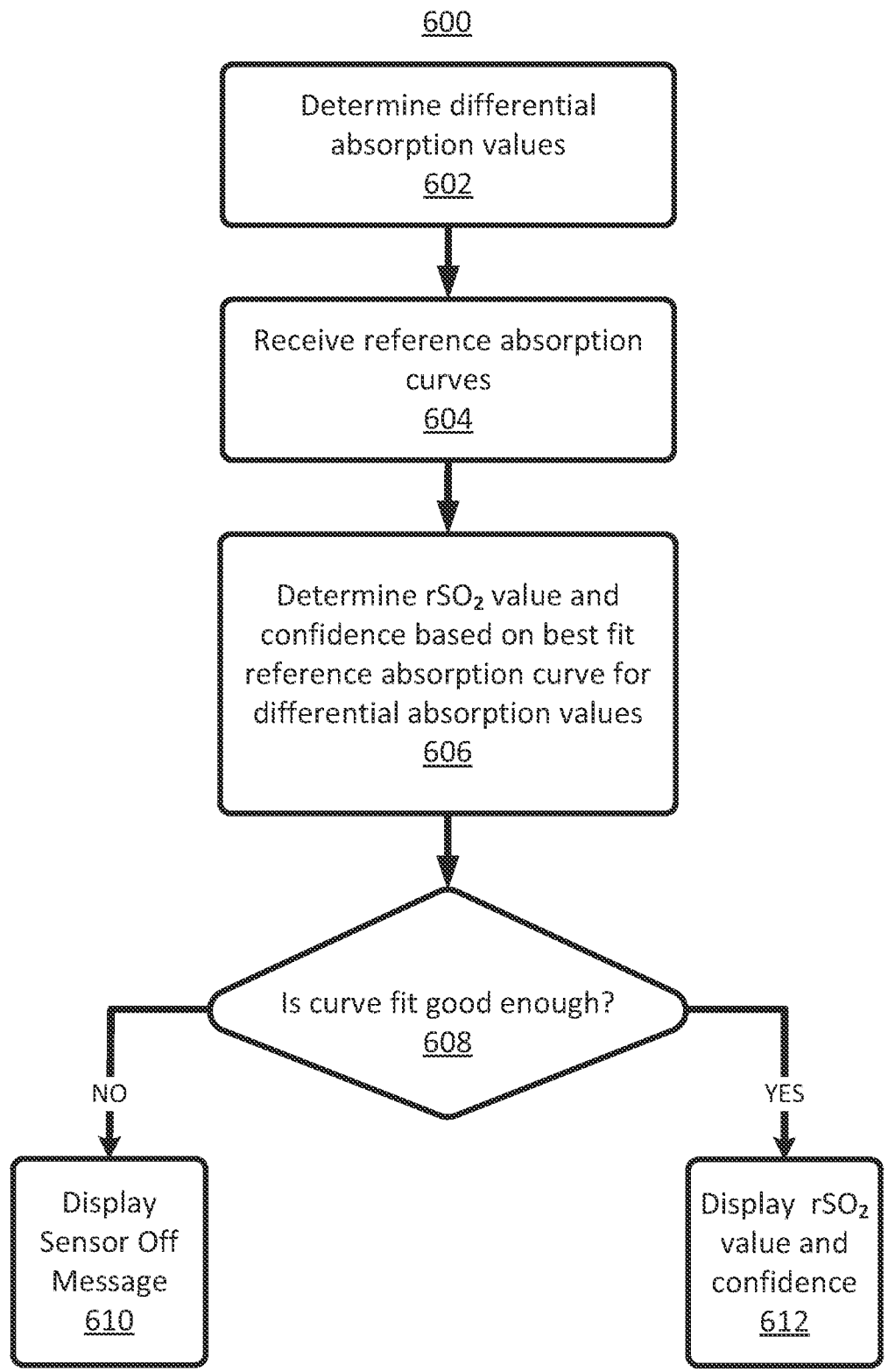
FIG. 6 shows an illustrative flow diagram including steps for determining an $rSO_2$ value using reference absorption sets in accordance with some embodiments of the present disclosure.

FIG. 6 shows an illustrative flow diagram 600 including steps for determining an $rSO_2$ value using reference absorption sets in accordance with some embodiments of the present disclosure.

At step 602, the processing equipment may determine differential absorption values for a subject. As discussed above, a differential absorption value may correspond to a difference in first and second absorption values, each corresponding to the same wavelength of light, computed for respective first and second regions of a subject's tissue. In some embodiments, the processing equipment may be implemented as part of a regional oximeter, and for each wavelength of light, the processing equipment may compare the amount of light absorbed by the subject's tissue in a first region to the amount of light absorbed by the subject's tissue in a second region to derive the differential absorption values. In some embodiments, the processing equipment may determine normalized absorption values based on the differential absorption values. In some embodiments, the processing equipment may create an absorption measurement vector $\vec{A}$ of absorption values:

$$\vec{A} = [A_1 \ A_2 \ldots A_m], \quad (3)$$

where m denotes the number of wavelengths of light for which absorption values are computed (i.e., in step 602 of FIG. 6). The absorption values in vector $\vec{A}$ may correspond to differential absorption values $\Delta A_{\lambda,i}$ computed using Eq. 1. In some embodiments, the differential absorption values may be determined from absorption values, first derivatives of absorption values, or higher order derivatives of absorption values. In some embodiments, the processing equipment may determine the first derivative or a higher order derivative of the differential absorption values.

At step 604, the processing equipment may receive reference absorption curves. In some embodiments, the processing equipment may receive reference sets of absorption data. It will be understood that reference sets of absorption data may be represented as reference absorption curves, and, as used herein, reference absorption curves includes the reference sets of absorption data that they represent. In some embodiments, the processing equipment may receive reference absorption curves from memory, for example, memory 174 of FIG. 1. In some embodiments, the processing equipment may receive reference absorption curves from a hospital information system. In some embodiments, the processing equipment may receive reference absorption curves based on operator input. In some embodiments, the received reference absorption curves may be based on absorption values, first derivatives of absorption values, or higher order derivatives of absorption values. In some embodiments, the processing equipment may determine the first derivative or a higher order derivative of the reference absorption curves.

At step 606, the processing equipment may determine an $rSO_2$ value and a confidence measure associated with the $rSO_2$ value based on a best fit reference absorption curve for the differential absorption values. In some embodiments, the processing equipment may determine a best fit reference absorption curve based on a comparison of the differential absorption values to the reference absorption curves. In some embodiments, each of the reference absorption curves may represent expected absorption values corresponding to an $rSO_2$ value, and the processing equipment may compare the differential absorption values to the expected absorption values for each reference curve to determine a best fit reference absorption curve. In some embodiments, the confidence measure may be determined based on a goodness of fit of the best fit reference absorption curve. In some embodiments, the processing of step 606 may be performed on the first derivative or a higher order derivative of the differential absorption values and the reference absorption curves. Some embodiments of step 606 are further discussed with reference to FIG. 7.

Figure 7:
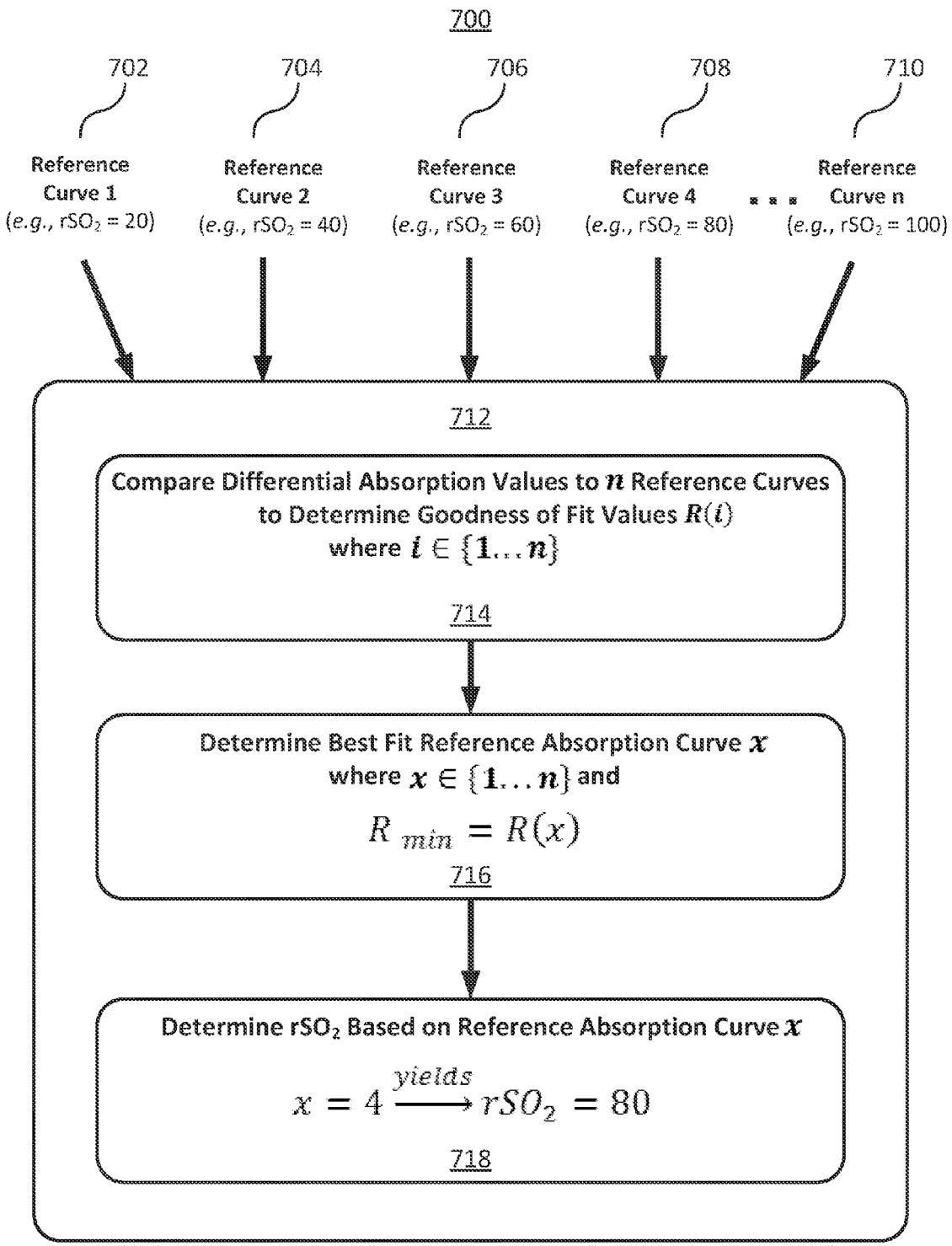
FIG. 7 shows an illustrative block diagram for determining an $rSO_2$ value using a best fit reference absorption curve in accordance with some embodiments of the present disclosure.

FIG. 7 shows an illustrative block diagram 700 for determining an $rSO_2$ value using a best fit reference absorption curve in accordance with some embodiments of the present disclosure. Processing block 712 may be implemented using any suitable processing equipment including, for example, processor 172 of FIG. 1. In some embodiments, processing block 712 may include comparison module 714, best fit module 716, and saturation module 718. Processing block 712 may receive any specified number of n reference curves (i.e., reference absorption curves). As depicted, processing block 712 receives n reference curves 702, 704, 706, 708, and 710. In some embodiments, reference curves 702, 704, 706, 708, and 710 may include any of the reference curves discussed with reference to FIG. 5. For example, reference curves 702, 704, 706, 708, and 710 may correspond, respectively, to reference absorption curves 506, 508, 510, 512, and 514 of FIG. 5. Each of reference curves 702, 704, 706, 708, and 710 may correspond to an $rSO_2$ value. As depicted, reference curves 702, 704, 706, 708, and 710 correspond, respectively, to rSO$_2$ values of 20, 40, 60, 80, and 100. In some embodiments, any number n of reference curves may be used. For example, the processing equipment may receive 100 reference curves, corresponding, respectively, to rSO$_2$ values from 1-100. It will be understood that reference curves 702, 704, 706, 708, and 710 are presented for purposes of illustration and not by way of limitation.

Comparison module 714 may compare differential absorption values to the n reference curves to determine goodness of fit values R(i), where i∈{1 ... n}, for each of the n reference curves. The goodness of fit values may be determined using any suitable measure for quantifying the discrepancy between the differential absorption values and the absorption data represented in reference curves 1-n, including, for example, correlation measures, coefficients of determination, least squares, Pearson's chi-squared test, any other suitable goodness of fit measure, or any combination thereof. In some embodiments, the goodness of fit values R(i) may be correlation measures. For example, the processing equipment may compare differential absorption values to reference curves 1-n to determine correlation measures for each of the reference curves. In some embodiments, the processing equipment may determine a correlation measure for each of reference curves 1-n based on a Pearson product-moment correlation coefficient. In some embodiments, the processing equipment may compare the absorption measurement vector $\vec{A}$, described in step 602 of FIG. 6, to reference curves 1-n to determined goodness of fit values R(i). In some embodiments, the processing equipment may store the absorption data of the n reference curves in a table with n rows, each row corresponding to one of the reference curves. The processing equipment may compare the absorption values of vector $\vec{A}$, defined in Eq. 3, to the absorption values in a row to obtain the goodness of fit value R(i) for that row.

Best fit module 716 may determine a best fit reference absorption curve x, where x∈{1 ... n}, from among the n reference curves, based on the goodness of fit values R(i) determined by comparison module 714. In some embodiments, the processing equipment may determine the best fit reference absorption curve x based on the correlation measures determined by comparison module 714. In some embodiments, the processing equipment may store the goodness of fit values R(i) determined by comparison module 714 in a vector $\vec{R}$. The processing equipment may determine the best fit reference absorption curve x based on the vector $\vec{R}$. For example, R(i) may be determined based on the Pearson product-moment correlation coefficients, and the processing equipment may determine the best fit reference absorption curve x based on the row associated with the minimum value R(x) in $\vec{R}$, denoted $R_{min}$. In some embodiments, the processing equipment may smooth vector $\vec{R}$ to remove any spurious minimums and determine $R_{min}$ based on the smoothed vector $\underline{R}$. In some embodiments, the processing equipment may determine $R_{min}$ based on an error minimization method. For example, the processing equipment may determine $R_{min}$ based on the Levenberg-Marguardt algorithm. It will be understood that the foregoing are provided by way of illustration, not by way of limitation, and that the processing equipment may use any suitable method or algorithm for determining $R_{min}$. It will be understood that $R_{min}$ is merely exemplary and that any suitable technique for determining a best fit reference absorption curve x based on the goodness of fit values R(i) may be used. Saturation module 718 may determine an rSO$_2$ value based on the best fit reference absorption curve x. For example, reference curve 708 may be determined to be the best fit reference absorption curve (i.e., x=4), and the processing equipment may determine an rSO$_2$ value of 80.

Referring back to FIG. 6, at step 606, the processing equipment may determine an rSO$_2$ value according saturation module 718 of FIG. 7. In some embodiments, the processing equipment may determine a confidence measure for the determined rSO$_2$ value based on $R_{min}$ determined by best fit module 716 of FIG. 7. It will be understood that the confidence measure may correspond to any suitable technique for representing the discrepancy between the differential absorption values and the reference absorption curves.

At step 608, the processing equipment may determine whether the curve fit is good enough to display the rSO$_2$ value. In some embodiments, the processing equipment may determine whether the curve fit is good enough based on the confidence measure associated with the rSO$_2$ value. In some embodiments, the processing equipment may compare the confidence measure determined in step 606 to a predetermined threshold. For example, the confidence measure may be $R_{min}$, and the processing equipment may determine if $R_{min}$ exceeds a predetermined threshold. The processing equipment may use any suitable technique for comparing the confidence measure to the predetermined threshold to determine if the confidence measure exceeds the predetermined threshold. In some embodiments, the confidence measure may exceed the predetermined threshold if it is determined to be equal to the predetermined threshold. In some embodiments the predetermined threshold may be adjustable based on user input. In some embodiments the processing equipment may receive the predetermined threshold from memory, for example, memory 174 of FIG. 1. The confidence measure can be displayed to the user in any suitable format. For example, the confidence measure may be displayed as a number, as a signal strength indicator type icon, as error bars around a trend graph, as the color of the rSO2 number or outline, in any other suitable format, or in any combination thereof. In some embodiments, one threshold may be used to prevent the display of physiological information and another threshold may be used to display physiological information with a reduced confidence indication. For example, if confidence is above a first relatively high threshold (e.g., indicating high confidence), the rSO2 value may be displayed normally. If confidence is below the first threshold, but above a second relatively lower threshold (e.g., indicating medium confidence), the rSO2 value may be displayed with a message that states "trending only," indicating that the number can be used to monitor rSO2 trend over time, but may not be an accurate measure of absolute regional saturation. If confidence is below the second threshold (e.g., indicating low confidence), physiological information may not be displayed.

When it is determined at step 608 that the curve fit for the best fit reference curve is not good enough, the processing equipment may, at step 610, display a sensor off message. In some embodiments, the processing equipment may sound an audible alarm using, for example, speaker 186 of FIG. 1. In some embodiments, the processing equipment may not display a sensor off message or an rSO$_2$ value. In some embodiments, the processing equipment may include other messages or indicators as described below, for example, in connection with step 816 of FIG. 8.

When it is determined at step 608 that the curve fit for best fit reference is good enough, the processing equipment may, at step 612, display the rSO$_2$ value. In some embodiments, the rSO$_2$ value may be displayed on display 184 of FIG. 1, display 328 of multi-parameter physiological monitor 326 or display 320 of monitor 314 of FIG. 3, or any other suitable display for depicting physiological information. In some embodiments, the processing equipment may determine more than one $rSO_2$ value for a subject over a period of time. The processing equipment may combine the $rSO_2$ values, for example, using an average, or a weighted average based on the respective confidence measures, to determine a final $rSO_2$ value for the subject. The processing equipment may display the final $rSO_2$ value, as described above. One or more of the foregoing steps of FIG. 6 may implemented as part of the overall flow diagram shown in FIG. 8, described below.

Figure 8:
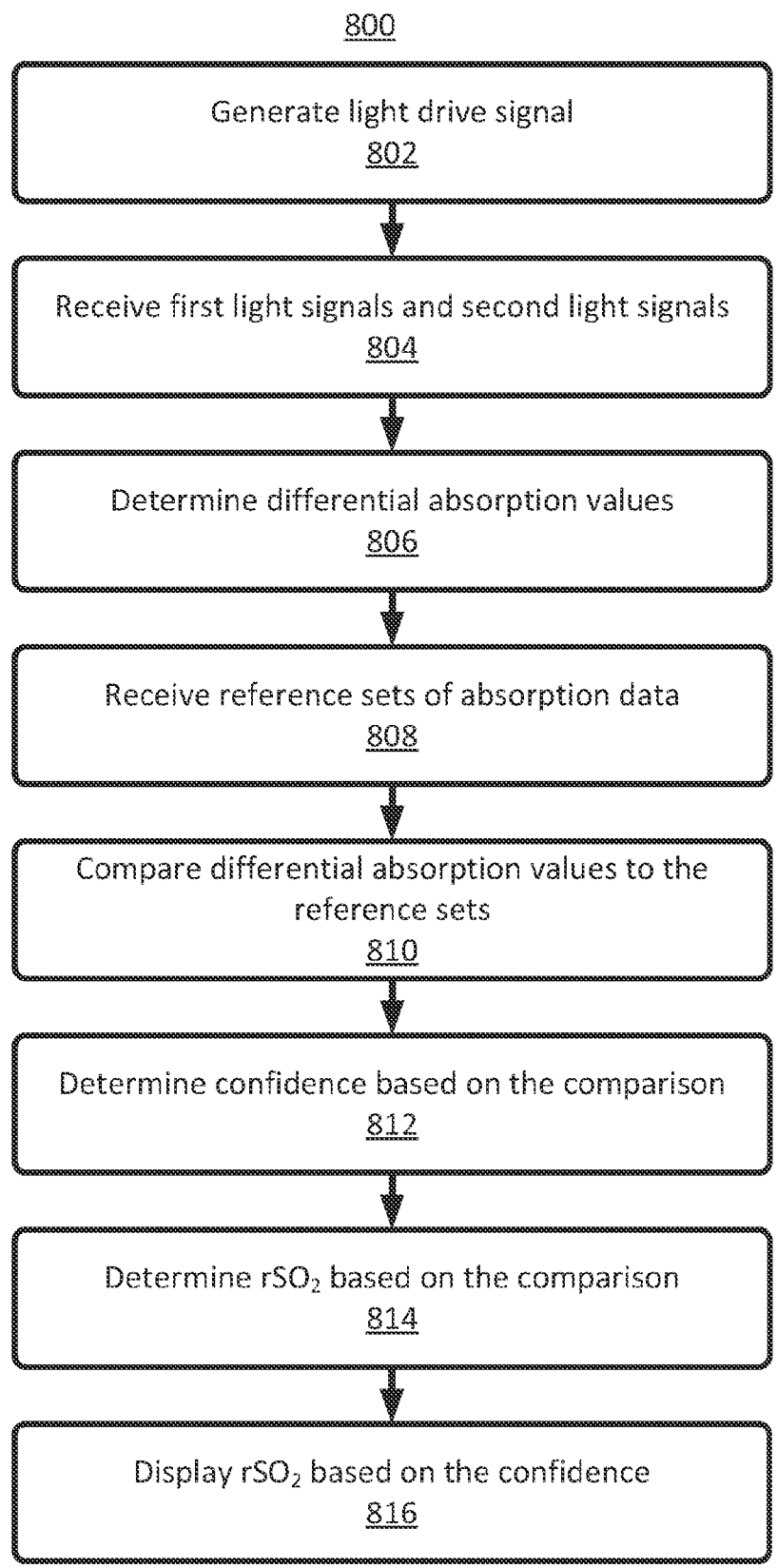
FIG. 8 shows an illustrative flow diagram including steps for determining an $rSO_2$ value using reference sets of absorption data in accordance with some embodiments of the present disclosure.

FIG. 8 shows an illustrative flow diagram 800 including steps for determining an $rSO_2$ value using reference sets of absorption data in accordance with some embodiments of the present disclosure.

At step 802, the processing equipment may generate a light drive signal configured to cause one or more light sources to emit light signals corresponding to wavelengths of light. In some embodiments, the one or more light sources may emit four wavelengths of light (e.g., 724 nm, 770 nm, 810 nm, and 850 nm) into a subject's tissue. This is merely illustrative and any suitable number of wavelengths of light and wavelength frequencies may be used. The one or more light sources may correspond to light source 130 of FIG. 1, 316 of FIG. 3, or 402 of FIG. 4. The light drive signal may correspond to the light drive signal shown in FIG. 2A.

At step 804, the processing equipment may receive first light signals corresponding to wavelengths of light that have been attenuated by a first region of a subject and second light signals corresponding to wavelengths of light that have been attenuated by a second region of the subject. In some embodiments, the first light signals may travel first mean path length 408 of FIG. 4 and the second light signals may travel to second mean path length 410 of FIG. 4. In some embodiments, the first signals may be received by a near detector, which may correspond to near detector 404 of FIG. 4, and the second signals may be received by a far detector, which may correspond to far detector 406 of FIG. 4. As described above, the first region may correspond to a smaller, shallow region of tissue than the second region, which may correspond to a larger, deep region of tissue. For example, the processing equipment may be implemented as part of a cerebral oximeter, where the first region may include the subject's outer skin, shallow tissue, cranial bone, Dura Mater, and shallow cerebral tissue and the second region may include all of the first region and the subject's deeper cerebral tissue.

At step 806, the processing equipment may determine differential absorption values, where each of the differential absorption values is based on a difference in absorption associated with the first and second regions of the subject for a respective wavelength of light. In some embodiments, the differential absorption values may be determined using Eq. 1, as described above. In some embodiments, the processing equipment may calculate a first, second, or higher derivative of the differential absorption values to generate derivative absorption values. The processing equipment may perform steps 810-816 using derivative absorption values instead of differential absorption values. By using derivative absorption values, the calculations will be more tolerant to losses that are linearly dependent on the wavelength.

At step 808, the processing equipment may receive reference sets of absorption data corresponding to different $rSO_2$ values. In some embodiments, the reference sets of absorption data may include reference absorption curves, as discussed above with respect to FIG. 6. For example the processing equipment may receive reference absorption curves corresponding to reference curves 702, 704, 706, 708, and 710 of FIG. 7 and/or reference absorption curves 506, 508, 510, 512, and 514 of FIG. 5. In some embodiments, reference sets may include reference templates, tables, arrays, curves, plots, any other suitable technique for representing absorption data, or any combination thereof. In some embodiments, the reference sets may include derivative absorption data. In some embodiments, the processing equipment may receive the reference sets of absorption data from memory, for example, memory 174 of FIG. 1.

At step 810, the processing equipment may compare the differential absorption values determined in step 806 to the reference sets received in step 808. In some embodiments, each of the reference sets includes expected absorption values corresponding to an $rSO_2$ value, and the processing equipment may compare the differential absorption values to the expected absorption values of each reference set. In some embodiments, the processing equipment may compare the differential absorption values to the reference sets to select a reference set. In some embodiments, the processing equipment may compare the differential absorption values to the reference absorption curves to determine a best fit reference absorption curve, as described above with reference to blocks 714 and 716 of FIG. 7. In some embodiments, the processing equipment may compare derivative absorption values to reference sets of derivative absorption data.

At step 812, the processing equipment may determine a confidence measure based on the comparison in step 810. In some embodiments, the confidence measure may be based on a goodness of fit value $R(x)$ associated with the best fit reference absorption curve x, as described above in reference to comparison module 714 and best fit module 716 of FIG. 7. For example, the confidence measure may correspond to the $R_{min}$ value, as described above in step 606 of FIG. 6. It will be understood that the confidence measure may correspond to any suitable technique for representing the discrepancy between the differential absorption values and the expected absorption values of the reference sets (i.e., reference absorption curves).

At step 814, the processing equipment may determine an $rSO_2$ value of the subject based on the comparison in step 810. In some embodiments, the processing equipment may select a reference set and determine an $rSO_2$ value of the subject based on the selected reference set. In some embodiments, the processing equipment may select a reference set based on the best fit reference absorption curve, as described above with reference to best fit module 716 of FIG. 7. In some embodiments the processing equipment may select a reference set associated with the best correlation measure. Correlation measures are discussed in detail above with reference to comparison module 714 of FIG. 7.

At step 816, the processing equipment may display the $rSO_2$ value determined in step 814 based on the confidence measure determined in step 812. In some embodiments, the processing equipment may determine whether or not to display the $rSO_2$ value based on whether the confidence measure is good enough. In some embodiments, the processing equipment may compare the confidence measure with a predetermined threshold, as described above with reference to step 608 of FIG. 6. In some embodiments, when it is determined that the confidence measure is too low (e.g., falls below the predetermined threshold), the processing equipment may disregard the $rSO_2$ value associated with the low confidence measure and continue displaying a previously determined $rSO_2$ value. In some embodiments, the processing equipment may continue displaying a previously determined $rSO_2$ value and display an indication of the low confidence measure (e.g., a warning or alert). In some embodiments, the processing equipment may discontinue displaying an $rSO_2$ value and display an indication of the low confidence measure. In some embodiments, the indication of the low confidence measure may be a sensor off message, as described above in step 610 of FIG. 6. In some embodiments, when it is determined that the confidence measure is high (e.g., falls exceeds a predetermined threshold), the processing equipment may display the $rSO_2$ value associated with the high confidence measure. In some embodiments, the displayed $rSO_2$ value may be a weighted average of previously determined $rSO_2$ values, weighted by their respective $R_{min}$ values. In some embodiments, the $R_{min}$ values may be displayed to indicate confidence or as a quality index. The $R_{min}$ values are a measure of how well the system is tracking the hemoglobin absorption curves. Therefore, the $R_{min}$ values may also be used as a confidence measure for any metric that is intended to track changes in hemoglobin, such as the blood volume index (BVI). In some embodiments, the processing equipment may display the $rSO_2$ value and the associated confidence measure, as described above in step 612 of FIG. 6. In some embodiments, step 816 may correspond to steps 608-612 of FIG. 6.

Figure 9:
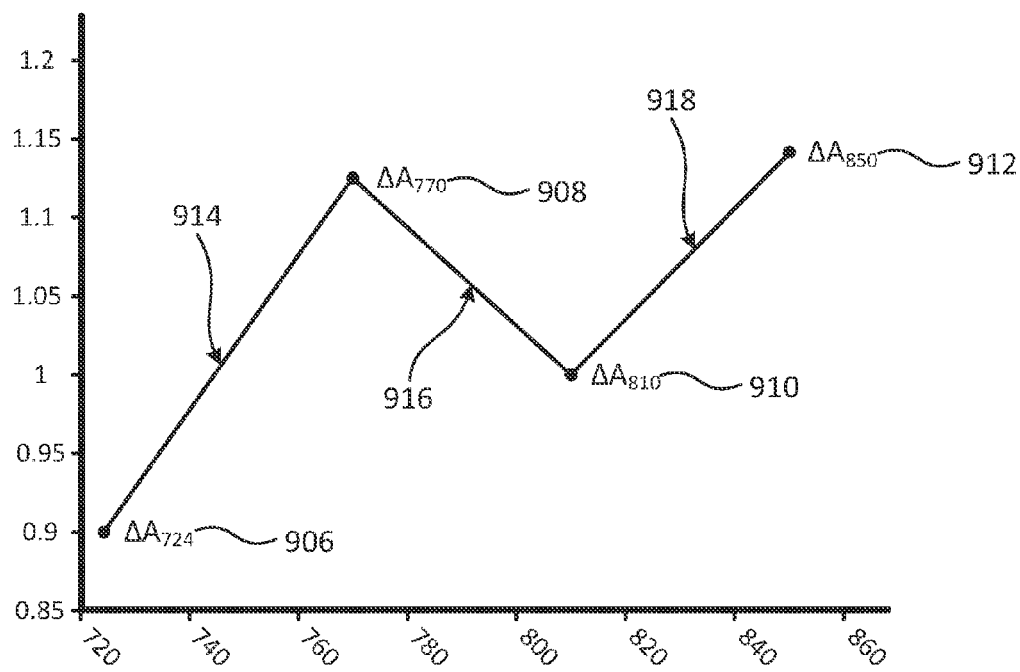
FIG. 9 shows an illustrative plot of absorption values in accordance with some embodiments of the present disclosure.
Figure 10:
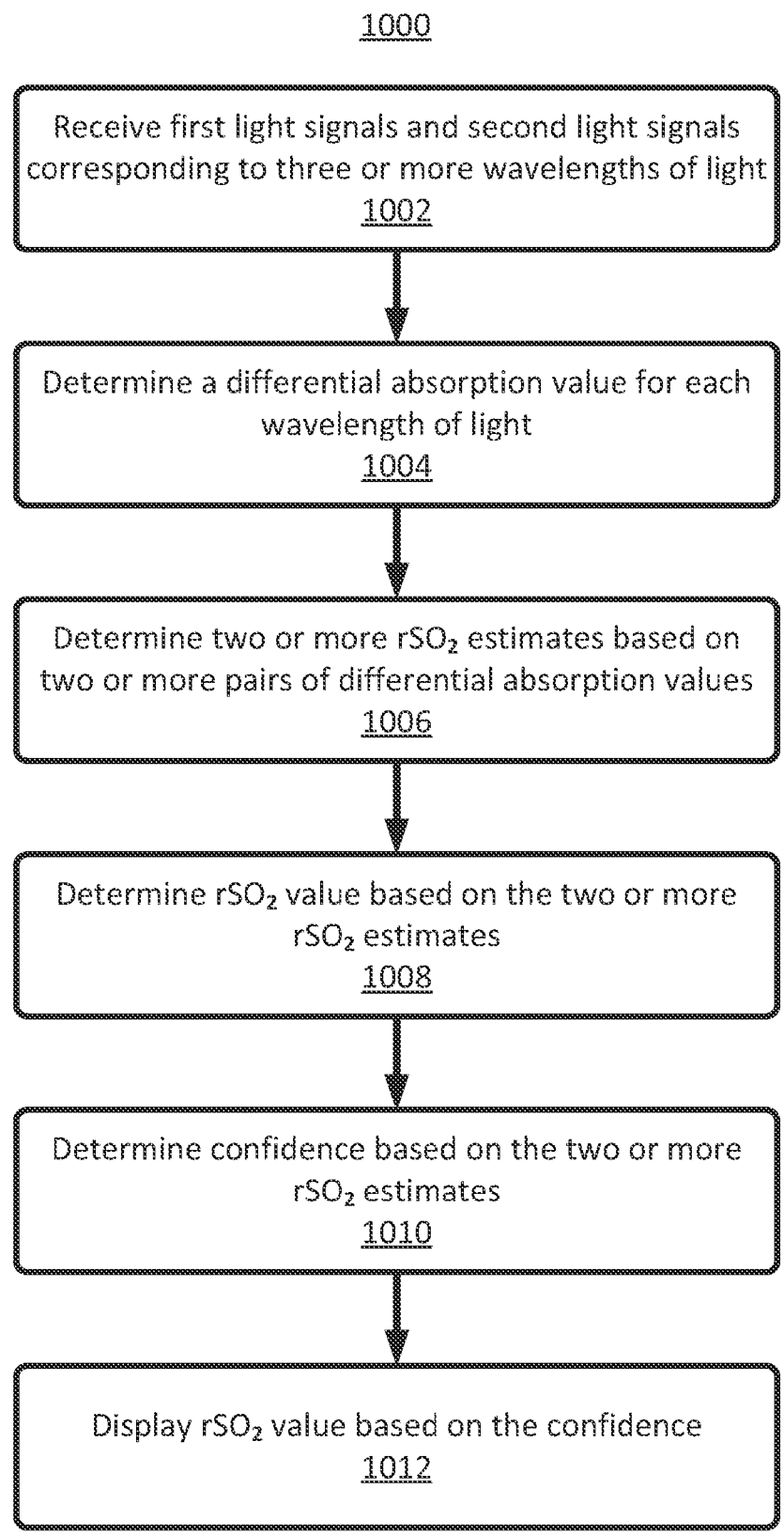
FIG. 10 shows an illustrative flow diagram including steps for determining an $rSO_2$ value using two or more $rSO_2$ estimates in accordance with some embodiments of the present disclosure.
Figure 11:
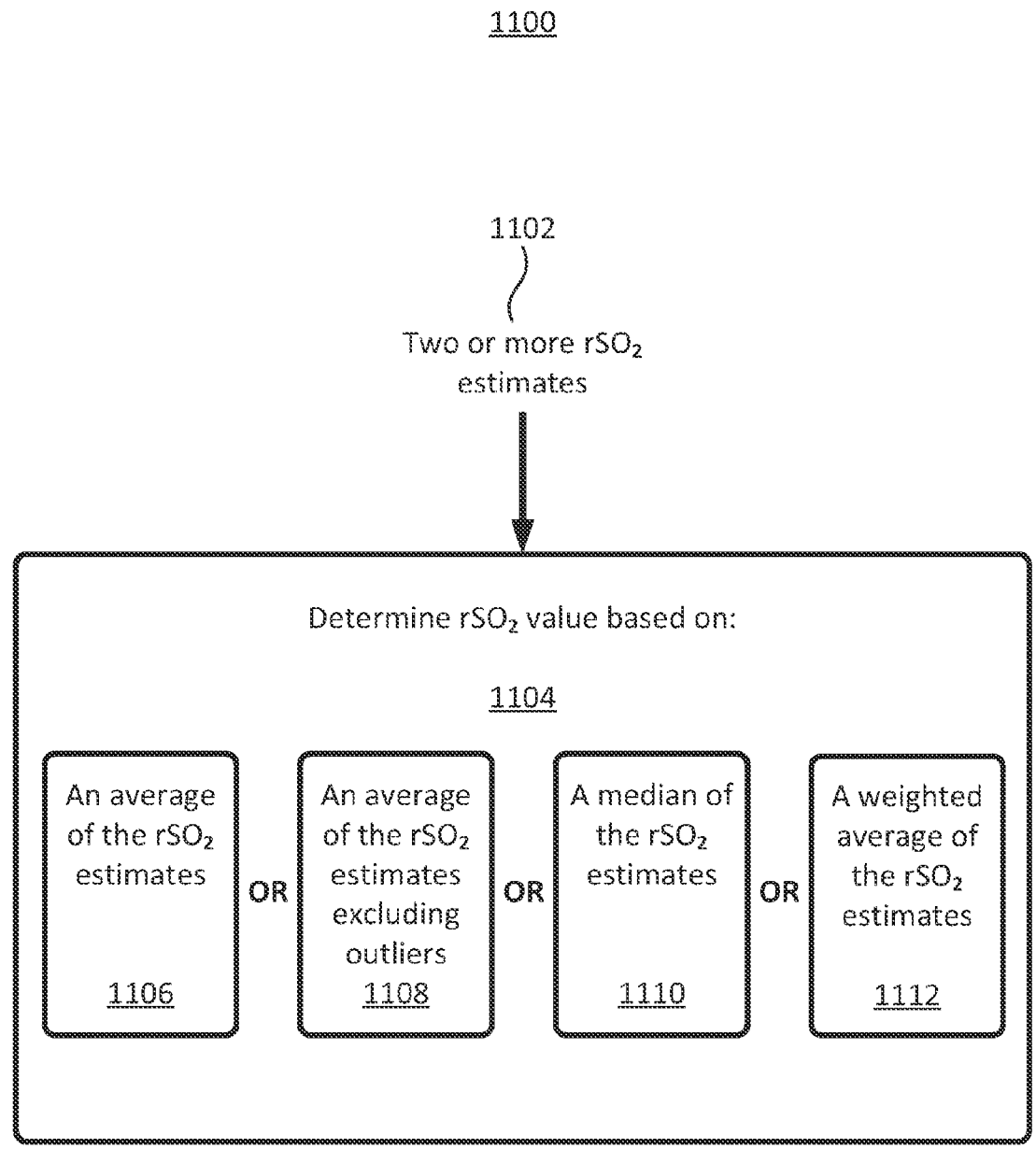
FIG. 11 shows an illustrative block diagram for determining an $rSO_2$ value using two or more $rSO_2$ estimates in accordance with some embodiments of the present disclosure.

It will be understood that the steps above are exemplary and that in some implementations, steps may be added, removed, omitted, repeated, reordered, modified in any other suitable way, or any combination thereof. For example, in some embodiments, step 812 may be removed and the $rSO_2$ values may be displayed without determining confidence. As described above, FIGS. 5-8 show determining an $rSO_2$ value of a subject using reference sets of absorption data. FIGS. 9-11, described below, show systems and methods for determining an $rSO_2$ value of a subject using two or more $rSO_2$ estimates based on two or more pairs of differential absorption values.

FIG. 9 shows an illustrative plot 900 of absorption values in accordance with some embodiments of the present disclosure. Vertical axis 902 of plot 900 corresponds to absorption values (e.g., normalized absorption values), indicative of the difference in the amount of light of a particular wavelength absorbed by first and second regions of a subject's tissue. Horizontal axis 904 of plot 900 corresponds to wavelengths of light in the near-infrared spectrum. Points 906, 908, 910, and 912 correspond to exemplary absorption values computed at four different wavelengths of light. Slopes 914, 916, and 918 are shown connecting points 906 and 908, points 908 and 910, and points 910 and 912, respectively.

In some embodiments, the processing equipment determines differential absorption values based on three or more wavelengths of light. In the illustrated embodiment, points 906, 908, 910, and 912 may correspond to the attenuation of light (i.e., absorption) determined for light signals corresponding to four wavelengths, 724 nm, 770 nm, 810 nm, and 850 nm, respectively. It will be understood that these wavelengths of light are merely exemplary, and that differential absorption values may be determined for any suitable wavelengths of light (e.g., wavelengths in the near-infrared spectrum). In some embodiments, the processing equipment may be implemented as part of a regional oximeter, and points 906, 908, 910, and 912 may correspond to differential absorption values calculated using Eq. 1, described above. In some embodiments, points 906, 908, 910, and 912 may correspond to points 516, 518, 520, and 522 of FIG. 5. In some embodiments, the processing equipment may determine two or more $rSO_2$ estimates based on two or more pairs of differential absorption values. In the illustrated embodiment, slopes 914, 916, and 918 may correspond to three $rSO_2$ estimates, each based on a pair of differential absorption values 906, 908, 910, and 912. Slope 914 may correspond to an $rSO_2$ estimate associated with two wavelengths of light (i.e., 724 and 770 nm), and $rSO_2$ estimate 914 may be determined based on the pair of differential absorption values 906 and 908. Slope 916 may correspond to an $rSO_2$ estimate associated with two wavelengths of light (i.e., 770 and 810 nm), and $rSO_2$ estimate 916 may be determined based on the pair of differential absorption values 908 and 910. Slope 918 may correspond to an $rSO_2$ estimate associated with two wavelengths of light (i.e., 810 and 850 nm), and $rSO_2$ estimate 918 may be determined based on the pair of differential absorption values 910 and 912. In some embodiments, the processing equipment may determine a subject's $rSO_2$ value based on two or more $rSO_2$ estimates. Determining an $rSO_2$ value using two or more $rSO_2$ estimates is discussed in further detail below, with reference to FIGS. 10-11.

FIG. 10 shows an illustrative flow diagram 1000 including steps for determining an $rSO_2$ value using two or more $rSO_2$ estimates in accordance with some embodiments of the present disclosure.

As described above, with reference to step 802 of FIG. 8, the processing equipment may first generate a light drive signal configured to cause one or more light sources to emit light signals corresponding to the three or more wavelengths of light. At step 1002, the processing equipment may receive first light signals and second light signals corresponding to three or more wavelengths of light that have been attenuated by respective first and second regions of the subject. In some embodiments, the first light signals may travel first mean path length 408 of FIG. 4 and the second light signals may travel to second mean path length 410 of FIG. 4. In some embodiments, the first signals may be received by a near detector, which may correspond to near detector 404 of FIG. 4, and the second signals may be received by a far detector, which may correspond to far detector 406 of FIG. 4. As described above, the first region may correspond to a smaller, shallow region of tissue than the second region, which may correspond to a larger, deep region of tissue. For example, the processing equipment may be implemented as part of a cerebral oximeter, where the first region may include the subject's outer skin, shallow tissue, cranial bone, Dura Mater, and shallow cerebral tissue, and the second region may include all of the first region and the subject's deeper cerebral tissue.

At step 1004, the processing equipment may determine a differential absorption value for each wavelength of light, where each of the differential absorption values is based on a difference in absorption associated with the first and second regions of the subject for a respective wavelength of light. In some embodiments, the differential absorption values may be determined using Eq. 1, as described above. In some embodiments, determining differential absorption values may correspond to step 806 of FIG. 8, described above. In some embodiments, the processing equipment may calculate second or higher derivatives of the differential absorption values to generate derivative absorption values. The processing equipment may perform step 1006 using derivative absorption values instead of differential absorption values.

At step 1006, the processing equipment may determine two or more $rSO_2$ estimates based on two or more pairs of differential absorption values determined in step 1004, where each of the rSO$_2$ estimates is associated with two wavelengths of light. In some embodiments, each of the rSO$_2$ estimates is associated with more than two wavelengths of light. For example, the processing equipment may receive first light signals and second light signals corresponding to four or more wavelengths of light that have been attenuated by respective first and second regions of the subject, as described above in step 1002, and at step 1004, the processing equipment may determine a differential absorption value for each of the four or more wavelengths of light. The processing equipment may determine two or more rSO$_2$ estimates, each associated with three or more wavelengths of light, based on sets of three or more differential absorption values. In some embodiments, the processing equipment may determine the two or more rSO$_2$ estimates based on a difference between the differential absorption values computed at various wavelengths. In some embodiments, the processing equipment may determine the two or more rSO$_2$ estimates based on a slope between points representing the differential absorption values at various wavelengths, as described above with reference to FIG. 9. In some embodiments, the processing equipment may determine the two or more rSO$_2$ estimates using:

$$rSO_{2\lambda,i,j} = m_{\lambda,i,j} \cdot \Delta A_{\lambda,i,j} + b_{\lambda,i,j} \quad (4)$$

where $\Delta A_{\lambda,i,j} = \Delta A_{\lambda,i} - \Delta A_{\lambda,j}$, and where $m_{\lambda,i,j}$ and $b_{\lambda,i,j}$ denote constants based on the molar absorption coefficients of oxygenated hemoglobin and deoxygenated hemoglobin for a given wavelength or wavelengths. In some embodiments, constants $m_{\lambda,i,j}$ and $b_{\lambda,i,j}$ may be empirically derived or fine-tuned based on phantoms or other experimental data. It will be understood that while eq. 4 assumes a linear relationship between rSO$_2$ and $\Delta A_{\lambda,i,j}$, this is non-limiting, and any suitable empirically-derived curve or mapping from $\Delta A_{\lambda,i,j}$ to rSO$_2$ may be used. For example, the two or more rSO$_2$ estimates may be determined based on reference absorption curves, as described above and shown in FIG. 5. In some embodiments, the processing equipment may store the coefficients in a lookup table, which it may use to determine rSO$_2$ estimates based on $\Delta A_{\lambda,i,j}$ values. In some embodiments, the processing equipment may determine the two or more rSO$_2$ estimates based on two or more pairs of derivative absorption values. For example, the processing equipment may determine each of the two or more rSO$_2$ estimates based on the second derivative of the absorption spectra, given by:

$$rSO_{2_{i,j,k}} = m_{\lambda,i,j,k} \cdot \Delta A_{\lambda,i,j,k} + b_{\lambda,i,j,k} \quad (5)$$

where $m_{\lambda,i,j,k}$ and $b_{\lambda,i,j,k}$ denote constants based on the molar absorption coefficients of oxygenated hemoglobin and deoxygenated hemoglobin for a given wavelength or wavelengths, where differential absorption values $\Delta A_{i,j}$ and $\Delta A_{j,k}$ are given by:

$$\Delta A_{i,j} = A_i - A_j \quad (5a)$$

$$\Delta A_{j,k} = A_j - A_k \quad (5b)$$

and where second derivative differential absorption value $\Delta A_{\lambda,i,j,k}$ is given by:

$$\Delta A_{\lambda,i,j,k} = \Delta A_{i,j} - \Delta A_{j,k} = A_i - 2A_j + A_k \quad (5c)$$

In some embodiments, constants $m_{\lambda,i,j,k}$ and $b_{\lambda,i,j,k}$ may be empirically derived or fine-tuned based on phantoms or other experimental data. In some embodiments, each of the two or more rSO$_2$ estimates determined using eq. 5 may minimize additional sources of loss that are linearly dependent on wavelength. In some embodiments, the processing equipment may determine each of the two or more rSO$_2$ estimates based on additional higher order derivatives (i.e., third or higher derivatives) of the absorption spectra.

At step 1008, the processing equipment may determine an rSO$_2$ value based on the two or more rSO$_2$ estimates determined in step 1006. In some embodiments, the processing equipment may determine an rSO$_2$ value based on a combination of the two or more rSO$_2$ estimates. Some embodiments of step 1008 are further discussed with reference to FIG. 11.

FIG. 11 shows an illustrative block diagram 1100 for determining an rSO$_2$ value using two or more rSO$_2$ estimates in accordance with some embodiments of the present disclosure. Processing block 1104 may be implemented using any suitable processing equipment including, for example, processor 172 of FIG. 1. Processing block 1104 may include combination modules 1106, 1108, 1110, and 1112. Processing block 1104 may receive two or more rSO$_2$ estimates 1102. In some embodiments, two or more rSO$_2$ estimates 1102 may correspond to the two or more rSO$_2$ estimates determined in step 1006 of FIG. 6. In some embodiments, processing block 1104 may determine an rSO$_2$ value based on two or more rSO$_2$ estimates 1102. In some embodiments, combination module 1106 may determine an rSO$_2$ value based on an average of two or more rSO$_2$ estimates 1102. In some embodiments, combination module 1108 may determine an rSO$_2$ value based on an average of two or more rSO$_2$ estimates 1102 with any outliers among two or more rSO$_2$ estimates 1102 removed from the average. In some embodiments combination module 1110 may determine an rSO$_2$ value based on a median of two or more rSO$_2$ estimates 1102. In some embodiments combination module 1112 may determine an rSO$_2$ value based on a weighted average of two or more rSO$_2$ estimates 1102. In some embodiments, the processing equipment may compute signal strength measures for two or more rSO$_2$ estimates 1102 based on the light signals received in step 1002. The processing equipment may assign weights to two or more rSO$_2$ estimates 1102 based on the signal strength measures and determine an rSO$_2$ value based on a weighted average of two or more rSO$_2$ estimates 1102. In some embodiments, the processing equipment may assign weights to two or more rSO$_2$ estimates 1102 based on the signal strength measures and a reference signal strength distribution. For example, the reference signal strength distribution may be a known distribution of signal strengths for a given subject population (e.g., an infant population or an adult population). It will be understood that the foregoing techniques for combining two or more rSO$_2$ estimates 1102 to determine an rSO$_2$ value are merely exemplary and that any other suitable technique may be used for combining the estimates.

Referring back to FIG. 10, at step 1010, the processing equipment may determine a confidence measure associated with the rSO$_2$ value determined in step 1008 based on the two or more rSO$_2$ estimates determined in step 1006. For example, the processing equipment may determine a confidence measure based on two or more rSO$_2$ estimates determined in step 1006 using eq. 5. Confidence measures may include any suitable measure of uncertainty associated with the determined rSO$_2$ value based on the two or more rSO$_2$ estimates, for example, standard deviation, range, interquartile range, any other suitable statistical measure of uncertainty, or any combination thereof.

At step 1012, the processing equipment may display the rSO$_2$ value determined in step 1008 based on the confidence measure determined in step 1010. In some embodiments, the processing equipment may determine whether to display the rSO$_2$ value based on the confidence measure. In some embodiments, the processing equipment may compare the confidence measure determined in step 1010 to a predetermined threshold. For example, the confidence measure may be based on the standard deviation of the two or more $rSO_2$ estimates, and the processing equipment may determine not to display the $rSO_2$ value if the confidence measure exceeds a predetermined threshold. The processing equipment may use any suitable technique for comparing the confidence measure to the predetermined threshold to determine if the confidence measure exceeds the predetermined threshold. In some embodiments, the confidence measure may exceed the predetermined threshold if it is determined to be equal to the predetermined threshold. In some embodiments the processing equipment may receive the predetermined threshold from memory, for example, memory 174 of FIG. 1. In some embodiments the predetermined threshold may be adjustable based on user input. In some embodiments the processing equipment may receive the predetermined threshold from a hospital information system.

In some embodiments, when it is determined that the confidence measure is too low (e.g., falls below the predetermined threshold), the processing equipment may disregard the $rSO_2$ value associated with the low confidence measure and continue displaying a previously determined $rSO_2$ value. In some embodiments, the processing equipment may continue displaying a previously determined $rSO_2$ value and display an indication of the low confidence measure (e.g., a warning or alert). In some embodiments, the confidence measure may be displayed as a quality index to the user. In some embodiments, the processing equipment may discontinue displaying an $rSO_2$ value and display an indication of the low confidence measure. In some embodiments, the indication of the low confidence measure may be a sensor off message, as described above in step 610 of FIG. 6. In some embodiments, when it is determined that the confidence measure is high (e.g., exceeds a predetermined threshold), the processing equipment may display the $rSO_2$ value associated with the high confidence measure. In some embodiments, the processing equipment may display the $rSO_2$ value and the associated confidence measure, as described above in step 612 of FIG. 6. In some embodiments, the confidence measure may be used as a quality measure for physiological parameters other than $rSO_2$. For example, a tight distribution of $rSO_2$ estimates may indicate that the processing equipment is tracking hemoglobin, and thus, the confidence measure may be used as a quality measure for physiological parameters that track changes in hemoglobin concentration, including, for example, the blood volume index (BVI). In some embodiments, the processing equipment may display the BVI based on the associated confidence measure. For example, the processing equipment may not display BVI when there is a large ambiguity in $rSO_2$ estimates as indicated by a low confidence measure. In some embodiments, the confidence measure may be used to alter the color, shape, or size of parameters derived from hemoglobin (e.g., rSO2 and BVI) to visually indicate the level of confidence in the displayed parameters.

It will be understood that the steps above are exemplary and that in some implementations, steps may be added, removed, omitted, repeated, reordered, modified in any other suitable way, or any combination thereof. For example, in some embodiments, step 1010 may be removed and the $rSO_2$ values may be displayed without determining confidence.

The foregoing is merely illustrative of the principles of this disclosure, and various modifications may be made by those skilled in the art without departing from the scope of this disclosure. The above-described embodiments are presented for purposes of illustration and not by way of limitation. The present disclosure also can take many forms other than those explicitly described herein. Accordingly, it is emphasized that this disclosure is not limited to the explicitly disclosed methods, systems, and apparatuses, but is intended to include variations to and modifications thereof, which are within the spirit of the following claims.

What is claimed:

1. A system for determining regional blood oxygen saturation ($rSO_2$) of a subject comprising:
   an oximeter configured for:
      generating a light drive signal configured to cause one or more light sources to emit a plurality of light signals, wherein the plurality of light signals corresponds to a plurality of wavelengths of light;
      receiving a first plurality of light signals that have been attenuated by a first region of the subject, wherein the first plurality of light signals corresponds to the plurality of wavelengths of light;
      determining a first plurality of absorption values corresponding to the first region of the subject, wherein each of the first plurality of absorption values corresponds to a respective one of the plurality of wavelengths of light;
      receiving a second plurality of light signals that have been attenuated by a second region of the subject, wherein the second plurality of light signals corresponds to the plurality of wavelengths of light;
      determining a second plurality of absorption values corresponding to the second region of the subject, wherein each of the second plurality of absorption values corresponds to a respective one of the plurality of wavelengths of light;
      determining a difference between each of the first plurality of absorption values and a respective one of the second plurality of absorption values to generate a plurality of differential absorption values corresponding, respectively, to the plurality of wavelengths of light;
      receiving reference sets of absorption data, wherein each of the reference sets corresponds to a different $rSO_2$ value and comprises expected absorption values for each of the plurality of wavelengths of light;
      comparing the plurality of differential absorption values to the expected absorption values of the reference sets;
      determining a best fit reference set of the reference sets based on the comparison; and
      determining the $rSO_2$ of the subject based on the determined best fit reference set.

2. The system of claim 1, wherein the oximeter is further configured for displaying the $rSO_2$ of the subject.

3. The system of claim 1, wherein the oximeter is further configured for calculating a derivative of the plurality of differential absorption values to generate a plurality of derivative absorption values; and wherein comparing the plurality of differential absorption values to the expected absorption values of the reference sets comprises comparing the plurality of derivative absorption values to the expected absorption values of the reference sets.

4. The system of claim 1, wherein comparing the plurality of differential absorption values to the expected absorption values of the reference sets comprises computing a correlation measure for each reference set based on a comparison of the respective expected absorption values to the plurality of differential absorption values.

5. The system of claim 4, wherein the correlation measure is based on a Pearson product-moment correlation coefficient.

6. The system of claim 4, wherein determining the best fit reference set comprises
selecting the reference set associated with the correlation measure corresponding to the best correlation between the expected absorption values of the reference sets and the plurality of differential absorption values and wherein
determining the $rSO_2$ of the subject based on the determined best fit reference set comprises determining the $rSO_2$ of the subject based on the $rSO_2$ value corresponding to the selected reference set.

7. The system of claim 6, wherein the oximeter is further configured for:
determining a confidence measure associated with the determined $rSO_2$ of the subject based on the correlation measure of the selected reference set;
comparing the confidence measure with a predetermined threshold; and
displaying the $rSO_2$ of the subject based on the comparison.

8. The system of claim 6, wherein the oximeter is further configured for:
determining a confidence measure associated with the determined $rSO_2$ of the subject based on the correlation measure of the selected reference set; and
displaying the confidence measure.

9. The system of claim 6, wherein the oximeter is further configured for determining a sensor off indication based on the correlation measure corresponding to the best correlation.

10. The system of claim 1, wherein the expected absorption values of the reference sets comprise empirically determined absorption values.

11. The system of claim 1, wherein the reference sets correspond to each possible $rSO_2$ value.

\* \* \* \* \*